(12) United States Patent
Kim et al.

(10) Patent No.: US 10,696,671 B2
(45) Date of Patent: Jun. 30, 2020

(54) IMIDAZO[1,2-A]PYRIDINE DERIVATIVES, METHODS FOR PREPARING THE SAME AND USE THEREOF

(71) Applicant: Jeil Pharmaceutical Co., Ltd., Seoul (KR)

(72) Inventors: Jeongmin Kim, Seongnam-si (KR); Hyunho Lee, Yongin-si (KR); Kwangwoo Chun, Yongin-si (KR); Chun-Ho Park, Yongin-si (KR); Eunsung Jang, Daejeon (KR); Yoonsun Park, Yongin-si (KR); Joseph Kim, Yongin-si (KR)

(73) Assignee: Jeil Pharmaceutical Co., Ltd., Seoul (KR)

(*) Notice: Subject to any disclaimer, the term of this patent is extended or adjusted under 35 U.S.C. 154(b) by 0 days.

(21) Appl. No.: 16/314,749

(22) PCT Filed: Jul. 4, 2017

(86) PCT No.: PCT/KR2017/007055
§ 371 (c)(1),
(2) Date: Jan. 2, 2019

(87) PCT Pub. No.: WO2018/008929
PCT Pub. Date: Jan. 11, 2018

(65) Prior Publication Data
US 2019/0152971 A1 May 23, 2019

(30) Foreign Application Priority Data
Jul. 5, 2016 (KR) .................. 10-2016-0085048

(51) Int. Cl.
C07D 471/04 (2006.01)
C07D 519/00 (2006.01)
A61P 1/04 (2006.01)

(52) U.S. Cl.
CPC .............. *C07D 471/04* (2013.01); *A61P 1/04* (2018.01); *C07D 519/00* (2013.01)

(58) Field of Classification Search
CPC ........ A61P 1/04; C07D 471/04; C07D 519/00
See application file for complete search history.

(56) References Cited

U.S. PATENT DOCUMENTS

| | | | |
|---|---|---|---|
| 4,920,129 A | 4/1990 | Shiokawa et al. | |
| 6,313,136 B1 * | 11/2001 | Amin | C07D 471/04 514/300 |
| 2014/0235666 A1 | 8/2014 | Dahlstrom | |

FOREIGN PATENT DOCUMENTS

| | | |
|---|---|---|
| EP | 0033094 A1 | 8/1981 |
| JP | 2002513024 | 5/2002 |
| KR | 10-0043134 | 5/2001 |
| RU | 2348634 | 3/2009 |
| WO | 1999/055705 | 11/1999 |
| WO | 1999/055706 | 11/1999 |
| WO | 2002/020523 | 3/2002 |
| WO | WO 2004/113339 | 12/2004 |
| WO | 2006/025716 | 3/2006 |
| WO | 2007/026916 | 3/2007 |

(Continued)

OTHER PUBLICATIONS

AU Examination Report for App No. AU 2017293271, dated Mar. 27, 2019 (3 pages).
ISA/KR, International Preliminary Report on Patentability and Written Opinion for PCT/KR2017/007055, dated Jan. 8, 2019 (9 pages).
RU Official Action for App No. RU 2019102925, dated Apr. 29, 2019 (With English translation) (8 pages).
RU Search Report for App No. RU 2019102925, dated Apr. 22, 2019 (With English translation) (4 pages).
ISA/KR, International Search Report for PCT/KR2017/007055 (Dec. 12, 2017).
Havu, N., Digestion, 1986, 35 (Suppl 1), 42-55.

(Continued)

*Primary Examiner* — Valerie Rodriguez-Garcia
(74) *Attorney, Agent, or Firm* — Fish & Richardson P.C.

(57) ABSTRACT

The present disclosure relates to novel imidazo[1,2-a]pyridine derivatives, and more particularly to imidazo[1,2-a]pyridine derivatives of Formula 1

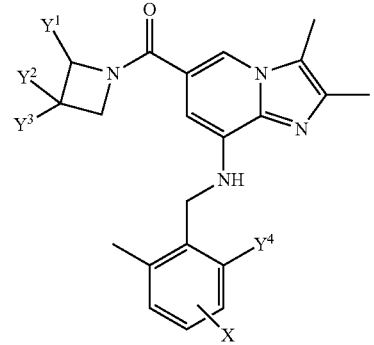

Formula 1 wherein
$Y^1$, $Y^2$ and $Y^3$ are each independently H, halogen, a $C_1$-$C_6$ straight chain alkyl unsubstituted or substituted with $R^1$, or hydroxy; $R^1$ is hydroxy; $Y^4$ is H, $C_1$-$C_6$ straight chain alkyl, or $C_1$-$C_6$ alkoxy; and X is H or halogen, and having an excellent activity of inhibiting gastric acid secretion, methods for preparing the same, and the use thereof. The imidazo[1,2-a]pyridine derivatives according to the present disclosure have gastric acid secretion inhibitory activity, and thus may be effectively used for the prevention or treatment of gastrointestinal inflammatory diseases or gastric acid-related diseases.

8 Claims, 1 Drawing Sheet

(56) References Cited

FOREIGN PATENT DOCUMENTS

| WO | 2007/039464 | | 4/2007 |
|---|---|---|---|
| WO | WO 2007/039464 | * | 4/2007 |
| WO | 2007/072146 | | 6/2007 |
| WO | WO 2008015196 | | 2/2008 |
| WO | WO/2018/008929 | | 1/2018 |

OTHER PUBLICATIONS

Chang Seok Song, Dong II Park, Korean J. med., 2011, 81(1), 6-10.
Yang YX, et al., JAMA, 2006, 296, 2947-53.
Targownik LE, et al., CMAJ, 2008, 179(4), 319-26.
Gray SL, et al., Arch Intern Med. 2010, 170(9), 765-71.
JP Official Action and Search Report for Pat App No. JP 2018-569003 dated Dec. 10, 2019, 6 pages (with English Translation).

* cited by examiner

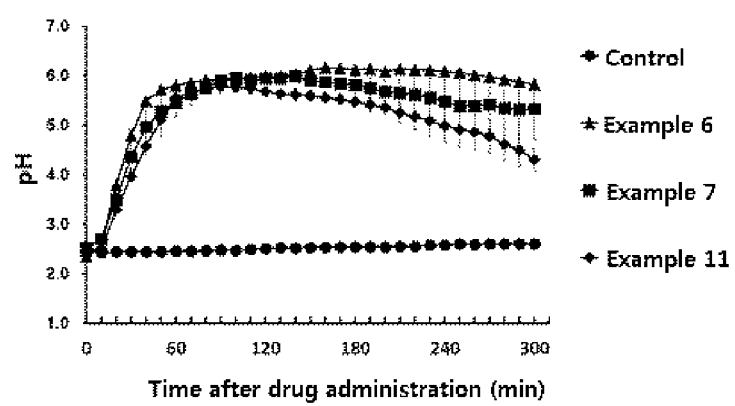

//
IMIDAZO[1,2-A]PYRIDINE DERIVATIVES, METHODS FOR PREPARING THE SAME AND USE THEREOF

TECHNICAL FIELD

The present disclosure relates to imidazo[1,2-α]pyridine derivatives that exhibit an excellent activity of inhibiting gastric acid secretion, methods for preparing the same, and the use thereof.

BACKGROUND ART

Gastrointestinal inflammatory diseases or gastric acid-related diseases, including peptic ulcer, gastric and duodenal ulcer, gastroesophageal reflux disease (GERD), nonerosive reflux disease (NERD) and the like, are the most common gastrointestinal diseases that affect most people in the world, including Korea.

Antiulcer agents, which are classified as agents for treating such diseases, are divided into two categories: drugs that inhibit aggressive factors such as gastric acid or pepsin; and drugs that enhance defensive factors such as sucralfate or misoprostol. Among these a representative therapeutic agents, various drugs have been used in the past as agent to inhibit aggressive factors such as antacids, anticholinergic drugs, $H_2$ receptor antagonists, proton pump inhibitors (PPIs) and the like. However, currently, proton pump inhibitor (PPI) drugs represented by Omeprazole, Lansoprazole, Pantoprazole, Raveprazole and the like are leading the market.

The proton pump is $H^+/K^+$-ATPase that releases $H^+$ into parietal cells and absorbs $K^+$ in the final stage of a gastric acid secretion response caused by binding of various acid secretion stimulators (histamine, acetylcholine, gastrin and the like) to their receptors present in parietal cells in vivo. Thus, proton pump inhibitors (PPIs) are drugs that inhibit gastric acid secretion by inhibiting the $H^+/K^+$-ATPase of parietal cells, which is the final stage of gastric acid secretion. These proton pump inhibitors (PPIs) are more effective and long-lasting in inhibiting gastric acid compared to prior drugs, and thus have been widely used for the past 20 years as therapeutic agents against peptic ulcer, gastric and duodenal ulcer, gastritis, gastroesophageal reflux disease (GERD) and the like. In particular, gastroesophageal reflux disease (GERD) is a chronic recurrent disease whose patients recently have rapidly increased in number, and it is an inflammatory disease that causes esophageal (adenocarcinoma) through the Barrett's esophagus when progressing to a chronic stage. The treatment rate of this gastroesophageal reflux disease (GERD) has increased rapidly since launching of proton pump inhibitors (PPIs).

However, it was reported that, since existing proton pump inhibitors (PPIs) are converted to an active sulfenamide form by acid secretion, and then bind irreversibly to the cysteine residues of $H^+/K^+$-ATPase to thereby inhibit gastric acid secretion for a long period of time, they may cause adverse effects, including gastric bacterial growth, stimulation of proton pump expression, and tumor cell formation due to hypergastrinemia [Havu N, *Digestion*, 1986, 35 (Suppl 1), 42-55; Chang Seok Song, Dong Il Park, Korean J Med., 2011, 81 (1), 6-10]. Furthermore, it was recently reported that, when these proton pump inhibitors (PPIs) are used over a long period of time, they inhibit calcium absorption ability and bone cell growth due to gastric acid inhibition, thereby increasing the risk of fractures of the hip joint, carpus and spine [Yang Y X, et al., *JAMA*, 2006, 296, 2947-53; Targownik L E, et al., CMAJ, 2008, 179 (4), 319-26; Gray S L, et al., *Arch Intern* Med. 2010, 170 (9), 765-71]. In addition, due to an increase in the elderly population, the use of nonsteroidal anti-inflammatory drugs (NSAIDs) has increased, and the development of various medical technologies has led to an increase in survival rate against various diseases, resulting in an increase in the number of patients with peptic ulcer and gastroesophageal reflux disease (GERD) induced by various causes. Furthermore, the number of patients refractory to proton pump inhibitors (PPIs) has also increased in spite of the very effective therapeutic ability of the proton pump inhibitors (PPIs).

Accordingly, among recent proton pump inhibitors (PPIs), there is an increasing interest and need for potassium competitive acid blocker (P-CAB, acid pump antagonist) drugs having a mechanism by which they bind reversibly to the $K^+$ binding site of $H^+/K^+$-ATPase to inhibit acid secretion in a potassium-competitive manner. Particularly, it is expected that unlike the irreversible proton pump inhibitors (PPIs), the reversible potassium competitive acid blockers (P-CABs) will exhibit fast efficacy in view of their mechanism, will be easily taken before or after a meal, and will be very effective in nighttime symptoms, which is a problem of irreversible proton pump inhibitors.

The present disclosure also relates to reversible proton pump inhibitors (P-CABs), and typical examples of reversible proton pump inhibitors known in the art include pyrrole derivative TAK-438 [Takeda Pharmaceutical Co. Ltd.; WO2007/026916], pyrrolo[2,3-c]pyridine YH-4808 [Yuhan Corp.; WO2006/025716], 1H-benzo[d]imidazole derivative CJ-12420 [Pfizer Inc., Japan, Raqualia Pharma Inc.; WO2007/072146], and imidazo[1,2-α]pyridine derivative AZD0865 [AstraZeneca AB; WO99/55705 and WO99/55706].

Accordingly, the present inventors have studied to develop low-molecular-weight reversible proton pump inhibitors that can be effectively used for the prevention or treatment of gastrointestinal inflammatory diseases or gastric acid-related diseases, including peptic ulcer, gastric and duodenal ulcer, gastritis, gastroesophageal reflux disease (GERD), nonerosive reflux disease (NERD) and the like. As a result, the present inventors have prepared novel imidazo[1,2-α]pyridine derivatives during such studies and have found that these derivatives exhibit excellent proton pump inhibitory activity, thereby completing the present disclosure.

DISCLOSURE OF INVENTION

Technical Problem

It is an object of the present disclosure to provide an imidazo[1,2-α]pyridine derivative having an excellent activity of inhibiting gastric acid secretion, and a method for preparing the same.

Another object of the present disclosure is to provide a pharmaceutical composition for preventing or treating a disease caused by excessive secretion of gastric acid, the composition containing the imidazo[1,2-α]pyridine derivative as an active ingredient.

Still another object of the present disclosure is to provide the use of the imidazo[1,2-α]pyridine derivative for prevention or treatment of a disease caused by excessive secretion of gastric acid.

Yet another object of the present disclosure is to provide a method for preventing or treating a disease caused by excessive secretion of gastric acid, the method comprising administering the imidazo[1,2-α]pyridine derivative.

Solution to Problem

To achieve the above objects, the present inventors have found that novel imidazo[1,2-α]pyridine derivatives are prepared and these derivatives are effective in the treatment of diseases caused by gastric acid excess secretion by inhibiting the secretion of gastric acid.

Imidazo[1,2-α]Pyridine Derivatives

The present disclosure provides an imidazo[1,2-α]pyridine derivative represented by the following formula 1 or a pharmaceutically acceptable salt thereof:

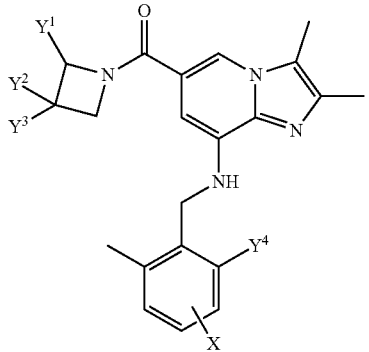

Formula 1 wherein $Y^1$, $Y^2$ and $Y^3$ are each independently H, halogen, $C_1$-$C_6$ straight or branched chain alkyl unsubstituted or substituted with $R^1$, hydroxy, $C_1$-$C_6$ alkoxy unsubstituted or substituted with $R^2$, or -A-B, or $Y^2$ and $Y^3$ may be bonded to each other to a form a 4- to 6-membered heterocyclic ring containing one or two heteroatoms selected from the group consisting of N, O and S;

$R^1$ and $R^2$ are each independently hydroxy or $C_1$-$C_6$ alkoxy;

A is —C(=O)—, —C(=O)O—, —OC(=O)—, or —S(=O)$_2$—;

B is H or $C_1$-$C_6$ straight or branched chain alkyl;

$Y^4$ is H, $C_1$-$C_6$ straight or branched chain alkyl, or $C_1$-$C_6$ alkoxy; and X is H or halogen.

According to one embodiment of the present disclosure, $Y^1$ may be H or $C_1$-$C_3$ straight or branched chain alkyl unsubstituted or substituted with $R^1$;

$Y^2$ and $Y^3$ are each independently H, F, Cl, $C_1$-$C_3$ straight or branched chain alkyl unsubstituted or substituted with $R^1$, hydroxy, $C_1$-$C_3$ alkoxy unsubstituted or substituted with $R^2$, or -A-B, or $Y^2$ and $Y^3$ may be bonded to each other to form a 4- to 6-membered heterocyclic ring containing one or two heteroatoms selected from the group consisting of N, O and S;

$R^1$ and $R^2$ may be each independently hydroxy or $C_1$-$C_3$ alkoxy;

A may be —C(=O)—, —C(=O)O—, —OC(=O)—, or —S(=O)$_2$—;

B may be $C_1$-$C_3$ straight or branched chain alkyl;

$Y^4$ may be H, $C_1$-$C_3$ straight or branched chain alkyl or $C_1$-$C_3$ alkoxy; and X may be H, F, or Cl.

According to another embodiment of the present disclosure, $Y^1$ may be H;

$Y^2$ and $Y^3$ may be each independently H, F, Cl, $C_1$-$C_2$ straight or branched chain alkyl unsubstituted or substituted with $R^1$, or hydroxy;

$R^1$ may be hydroxy;

$Y^4$ may be H or $C_1$-$C_2$ straight or branched chain alkyl; and

X may be H or F.

According to still another embodiment of the present disclosure, $Y^1$ may be H;

$Y^2$ and $Y^3$ may be each independently H, F, methyl, hydroxymethyl, or hydroxy;

$Y^4$ may be H or methyl; and

X may be H or F.

In a preferred embodiment, the imidazo[1,2-α]pyridine derivative of the present disclosure may be selected from the group consisting of the following compounds:

1) {8-[(2,6-dimethylbenzyl)amino]-2,3-dimethylimidazo[1,2-α]pyridin-6-yl}(3-hydroxyazetidin-1-yl)methanone;
2) 1-{8-[(2,6-dimethylbenzyl)amino]-2,3-dimethylimidazo[1,2-α]pyridine-6-carbonyl}azetidin-3-yl acetate;
3) {8-[(2,6-dimethylbenzyl)amino]-2,3-dimethylimidazo[1,2-α]pyridin-6-yl}(3-methoxyazetidin-1-yl)methanone;
4) {8-[(2,6-dimethylbenzyl)amino]-2,3-dimethylimidazo[1,2-α]pyridin-6-yl}(3-ethoxyazetidin-1-yl)methanone;
5) {8-[(2,6-dimethylbenzyl)amino]-2,3-dimethylimidazo[1,2-α]pyridin-6-yl}[3-(2-methoxyethoxy)azetidin-1-yl]methanone;
6) azetidin-1-yl{8-[(2,6-dimethylbenzyl)amino]-2,3-dimethylimidazo[1,2-α]pyridin-6-yl}methanone;
7) {8-[(2,6-dimethylbenzyl)amino]-2,3-dimethylimidazo[1,2-a]pyridin-6-yl}(3-fluoroazetidin-1-yl)methanone;
8) {8-[(2,6-dimethylbenzyl)amino]-2,3-dimethylimidazo[1,2-α]pyridin-6-yl}(3-methylazetidin-1-yl)methanone;
9) {8-[(2,6-dimethylbenzyl)amino]-2,3-dimethylimidazo[1,2-α]pyridin-6-yl}(3-hydroxy-3-methylazetidin-1-yl)methanone;
10) methyl 1-{8-[(2,6-dimethylbenzyl)amino]-2,3-dimethylimidazo[1,2-α]pyridine-6-carbonyl}azetidine-3-carboxylate;
11) {8-[(2,6-dimethylbenzyl)amino]-2,3-dimethylimidazo[1,2-α]pyridin-6-yl}[3-(hydroxymethyl)azetidin-1-yl]methanone;
12) {8-[(2,6-dimethylbenzyl)amino]-2,3-dimethylimidazo[1,2-α]pyridin-6-yl}[3-(methoxymethyl)azetidin-1-yl]methanone;
13) {8-[(2,6-dimethylbenzyl)amino]-2,3-dimethylimidazo[1,2-α]pyridin-6-yl}[3-fluoro-3-(hydroxymethyl)azetidin-1-yl]methanone;
14) {8-[(2,6-dimethylbenzyl)amino]-2,3-dimethylimidazo[1,2-α]pyridin-6-yl}[3-(hydroxymethyl)-3-methylazetidin-1-yl]methanone;
15) {8-[(2,6-dimethylbenzyl)amino]-2,3-dimethylimidazo[1,2-α]pyridin-6-yl}[3-(1-hydroxyethyl)azetidin-1-yl]methanone;
16) {8-[(2,6-dimethylbenzyl)amino]-2,3-dimethylimidazo[1,2-α]pyridin-6-yl}[3-(2-hydroxypropan-2-yl)azetidin-1-yl]methanone;
17) {8-[(2,6-dimethylbenzyl)amino]-2,3-dimethylimidazo[1,2-α]pyridin-6-yl}[2-(hydroxymethyl)azetidin-1-yl]methanone;

18) 1-{1-[8-({2,6-dimethylbenzyl}amino)-2,3-dimethylimidazo[1,2-α]pyridine-6-carbonyl]azetidin-3-yl}ethanone;
19) {8-[(2,6-dimethylbenzyl)amino]-2,3-dimethylimidazo[1,2-α]pyridin-6-yl}[3-(methylsulfonyl)azetidin-1-yl]methanone;
20) {8-[(2,6-dimethylbenzyl)amino]-2,3-dimethylimidazo[1,2-α]pyridin-6-yl}[3-(2-hydroxyethyl)azetidin-1-yl]methanone;
21) {8-[(2,6-dimethylbenzyl)amino]-2,3-dimethylimidazo[1,2-α]pyridin-6-yl}(2,6-diazaspiro[3.3]heptan-2-yl)methanone;
22) {8-[(2,6-dimethylbenzyl)amino]-2,3-dimethylimidazo[1,2-α]pyridin-6-yl}(2-oxa-6-azaspiro[3.3]heptan-6-yl)methanone;
23) {2,3-dimethyl-8-[(2-methylbenzyl)amino]imidazo[1,2-α]pyridin-6-yl}(3-hydroxyazetidin-1-yl)methanone;
24) {8-[(5-fluoro-2-methylbenzyl)amino]-2,3-dimethylimidazo[1,2-α]pyridin-6-yl}(3-hydroxyazetidin-1-yl)methanone;
25) (3-hydroxyazetidin-1-yl){8-[(2-methoxy-6-methylbenzyl)amino]-2,3-dimethylimidazo[1,2-α]pyridin-6-yl}methanone;
26) [3-(hydroxymethyl)azetidin-1-yl]{8-[(2-methoxy-6-methylbenzyl)amino]-2,3-dimethyl imidazo[1,2-α]pyridin-6-yl}methanone;
27) {8-[(4-fluoro-2-methylbenzyl)amino]-2,3-dimethylimidazo[1,2-α]pyridin-6-yl}(3-hydroxyazetidin-1-yl)methanone;
28) azetidin-1-yl {8-[(4-fluoro-2-methylbenzyl)amino]-2,3-dimethylimidazo[1,2-α]pyridin-6-yl}methanone;
29) {8-[(4-fluoro-2-methylbenzyl)amino]-2,3-dimethylimidazo[1,2-α]pyridin-6-yl}(3-fluoroazetidin-1-yl)methanone;
30) {8-[(4-fluoro-2-methylbenzyl)amino]-2,3-dimethylimidazo[1,2-α]pyridin-6-yl}(3-methylazetidin-1-yl)methanone;
31) {8-[(4-fluoro-2-methylbenzyl)amino]-2,3-dimethylimidazo[1,2-α]pyridin-6-yl}(3-hydroxy-3-methylazetidine-1-yl)methanone;
32) {8-[(2,6-dimethylbenzyl)amino]-2,3-dimethylimidazo[1,2-α]pyridin-6-yl}(3-methoxy-3-methylazetidin-1-yl)methanone;
33) {8-[(4-fluoro-2-methylbenzyl)amino]-2,3-dimethylimidazo[1,2-α]pyridin-6-yl}(3-(hydroxymethyl)azetidin-1-yl)methanone;
34) {8-[(4-fluoro-2,6-dimethylbenzyl)amino]-2,3-dimethylimidazo[1,2-α]pyridin-6-yl}(3-hydroxyazetidin-1-yl)methanone;
35) azetidin-1-yl{8-[(4-fluoro-2,6-dimethylbenzyl)amino]-2,3-dimethylimidazo[1,2-α]pyridin-6-yl}methanone;
36) {8-[(4-fluoro-2,6-dimethylbenzyl)amino]-2,3-dimethylimidazo[1,2-α]pyridin-6-yl}(3-fluoroazetidin-1-yl)methanone;
37) {8-[(4-fluoro-2,6-dimethylbenzyl)amino]-2,3-dimethylimidazo[1,2-α]pyridin-6-yl}(3-methylazetidin-1-yl)methanone;
38) {8-[(4-fluoro-2,6-dimethylbenzyl)amino]-2,3-dimethylimidazo[1,2-α]pyridin-6-yl}(3-hydroxy-3-methylazetidin-1-yl)methanone;
39) {8-[(4-fluoro-2,6-dimethylbenzyl)amino]-2,3-dimethylimidazo[1,2-α]pyridin-6-yl}[3-(hydroxymethyl)azetidin-1-yl]methanone;
40) {8-[(4-fluoro-2,6-dimethylbenzyl)amino]-2,3-dimethylimidazo[1,2-α]pyridin-6-yl}[3-(methoxymethyl)azetidin-1-yl]methanone;
41) {8-[(3-fluoro-2,6-dimethylbenzyl)amino]-2,3-dimethylimidazo[1,2-α]pyridin-6-yl}(3-hydroxyazetidin-1-yl)methanone;
42) azetidin-1-yl{8-[(3-fluoro-2,6-dimethylbenzyl)amino]-2,3-dimethylimidazo[1,2-α]pyridin-6-yl}methanone;
43) {8-[(3-fluoro-2,6-dimethylbenzyl)amino]-2,3-dimethylimidazo[1,2-α]pyridin-6-yl}(3-fluoroazetidin-1-yl)methanone;
44) {8-[(3-fluoro-2,6-dimethylbenzyl)amino]-2,3-dimethylimidazo[1,2-α]pyridin-6-yl}[3-(hydroxymethyl)azetidin-1-yl]methanone;
45) azetidin-1-yl{8-[(3-chloro-2,6-dimethylbenzyl)amino]-2,3-dimethylimidazo[1,2-α]pyridin-6-yl}methanone;
46) {8-[(3-chloro-2,6-dimethylbenzyl)amino]-2,3-dimethylimidazo[1,2-α]pyridin-6-yl}[(3-hydroxyazetidin-1-yl]methanone;
47) {8-[(3-chloro-2,6-dimethylbenzyl)amino]-2,3-dimethylimidazo[1,2-α]pyridin-6-yl}(3-fluoroazetidin-1-yl)methanone; and
48) {8-[(3-chloro-2,6-dimethylbenzyl)amino]-2,3-dimethylimidazo[1,2-α]pyridin-6-yl}[3-(hydroxymethyl)azetidin-1-yl]methanone.

In the present disclosure, pharmaceutically acceptable salts may be those that are generally used in the art such as acid addition salts that are formed by pharmaceutically acceptable free acids, but not limited thereto. The pharmaceutically acceptable free acids may be organic acids and inorganic acids. The inorganic acids may include hydrochloric acid, phosphoric acid, sulfuric acid, nitric acid and the like, and the organic acid may include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vinylic acid and the like.

Furthermore, a pharmaceutically acceptable metal salt may be prepared using a base. For example, an alkali metal or alkaline earth metal salt of a compound may be prepared by dissolving the compound in an excess of an alkali metal hydroxide or alkaline earth metal hydroxide solution, filtering an undissolved compound salt, and evaporating and drying the filtrate. Herein, a pharmaceutically acceptable metal salt suitable for pharmaceutical use is sodium, potassium or calcium salt, but is not limited thereto.

In addition, the compounds of formula 1 according to the present disclosure include solvates and hydrates that can be prepared from pharmaceutically acceptable salts, and all possible optical isomers, stereoisomers and mixtures thereof also fall within the scope of the present disclosure. Herein, solvates, hydrates and stereoisomers of the compounds represented by formula 1 may be prepared using conventional methods known in the art.

In addition, the compound of formula 1 according to the present disclosure may be prepared in a crystalline form or an amorphous form. When the compound of formula 1 is prepared in a crystalline form, it may optionally be hydrated or solvated.

Methods for Preparation of Imidazo[1,2-α]Pyridine Derivatives

The present disclosure provides methods for preparation of the imidazo[1,2-α]pyridine derivatives represented by formula 1 or pharmaceutically acceptable salts thereof.

Preferably, the compounds of formula 1 can be prepared by the method shown in reaction scheme 1 below, but are not limited thereto. Particularly, any person skilled in the art will sufficiently understand that the compounds of formula 1 according to the present disclosure can be prepared by various methods using known techniques well known in the art.

Reaction scheme 1 shown below show each step of a method for preparing representative compounds according to the present disclosure, and various compounds according to the present disclosure can be prepared by modifications that change reagents, solvents and reaction sequences, which are used in the preparation process shown in reaction scheme 1 below. Several compounds according to the present disclosure can be prepared according to processes that do not fall within the scope of reaction scheme 1 shown below, and specific processes for preparation of such compounds will be described in detail in the Examples below.

Preparation Method 1

Specifically, as shown in reaction scheme 1 below, the derivatives of formula 1 or pharmaceutically acceptable salts thereof can be prepared by a method comprising the steps of:

1) benzylating a carboxylic acid alkyl ester of formula 2 with substituted benzyl halide or benzaldehyde to thereby prepare a compound of formula 3 (step 1);

2) adding an aqueous solution of potassium hydroxide or sodium hydroxide dropwise to the compound of formula 3 prepared in step 1, thereby preparing a hydrolyzed carboxylic acid of formula 4 (step 2); and 3) amidating the carboxylic acid of formula 4, prepared in step 2, with unsubstituted or substituted azetidine by use of a coupling reagent, thereby preparing the compound of formula 1.

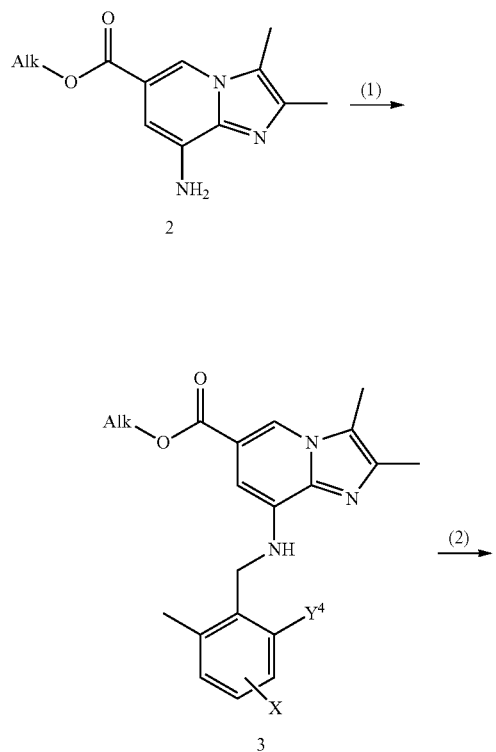

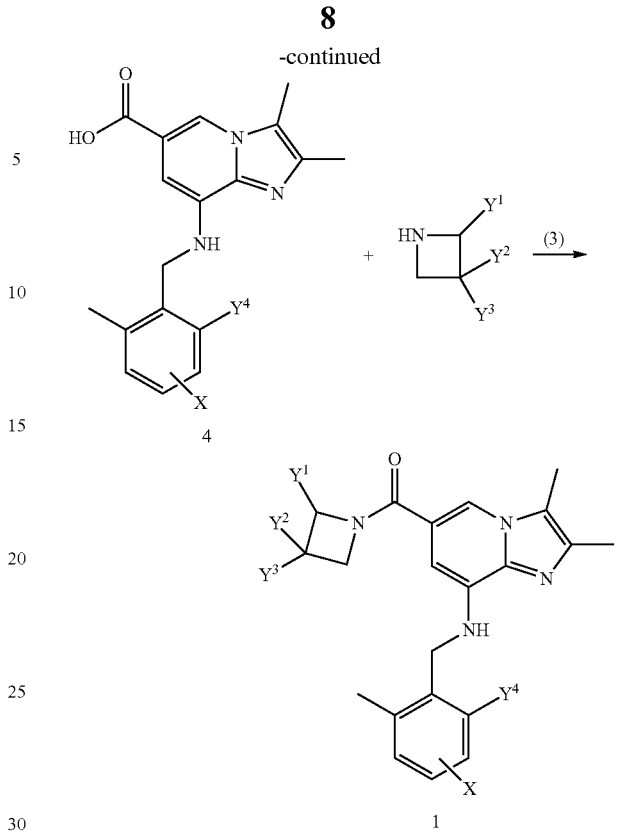

(wherein $Y^1$ to $Y^4$ and X are as defined in formula 1 above, and Alk is an alkyl group such as methyl, ethyl, isopropyl or the like. Preferably, Alk is isopropyl.)

Each of the method for preparing the compound of formula 1 will now be described in detail with reference to reaction scheme 1.

In step 1, a carboxylic acid alkyl ester of formula 2, which can be easily synthesized using a known technique (WO 99/055705 or WO 99/055706), is reacted with substituted benzyl halide (e.g., 2,6-dimethylbenzyl chloride or 4-fluoro-2-methylbenzyl bromide) in the presence of a base such as potassium carbonate and a catalytic amount of sodium iodide, thereby preparing a substituted benzylamino imidazolopyridine compound of formula 3. This reaction is benzylation of amine acid compound with benzyl halide and is performed in the presence of a base that may be used in benzylation. Examples of a base that may be used for this purpose include sodium hydride (NaH), potassium carbonate, sodium carbonate, cesium carbonate, sodium or potassium alkoxides, etc. In addition, the reaction is preferably performed in the presence of a solvent that does not adversely affect the reaction, and examples of this solvent include dichloromethane, chloroform, tetrahydrofuran, diethylether, toluene, N,N-dimethylformamide or acetonitrile. The reaction temperature is not particularly limited, but the reaction may generally be performed at cold temperature or warm temperature, preferably room temperature or warm temperature.

In step 2, an aqueous solution of potassium hydroxide or sodium hydroxide is slowly added dropwise to the compound of formula 3 prepared in step 1, thereby preparing a hydrolyzed carboxylic acid compound of formula (4). The reaction in step 2 is performed in an alcohol solvent such as methanol or ethanol, which does not adversely affect the reaction. The reaction temperature is not particularly limited, but the reaction is performed at cold temperature or warm temperature, preferably room temperature or warm temperature. This reaction may be performed under general ester hydrolysis conditions.

In step 3, the carboxylic acid compound of formula 4, prepared in step 2, is amidated with unsubstituted or substituted azetidine by use of a coupling reagent, thereby preparing the compound of formula 1. The coupling reagent used may be [1-(3-dimethylaminopropyl)-3-ethylcarbodiimide] (EDCI), 1,3-dicyclohexyl carbodiimide (DCC), 1,1-carbonyl diimidazole and the like, which is commercially easily available. Although this reaction may be performed in the absence of a base, it is preferably performed in a solvent, such as acetonitrile, dimethyl formamide or dichloromethane, which does not adversely affect the reaction, in the presence of a conventional base such as 4-dimethylaminopyridine, pyridine, triethylamine, diethylisopropylamine, N-methylmorpholine or dimethylphenylamine, which may be used in amidation. The reaction temperature is not particularly limited, but the reaction is performed at cold temperature or warm temperature, preferably room temperature or warm temperature.

Target compounds produced according to the method shown in reaction scheme 1 above may be purified using conventional methods, for example, column chromatography, recrystallization and the like.

The compounds of formula 1 according to the present disclosure may be prepared into pharmaceutically acceptable salts thereof or solvates thereof according to conventional methods known in the art.

Pharmaceutical Composition Containing Imidazo[1,2-α] Pyridine Derivative, Use Thereof, and Method for Treating Disease Using the Same The present disclosure provides a pharmaceutical composition for preventing or treating a disease caused by excessive secretion of gastric acid, the composition containing the imidazo[1,2-α]pyridine derivative of formula 1 or a pharmaceutically acceptable salt thereof.

Examples of the disease caused by excessive secretion of gastric acid include gastrointestinal inflammatory diseases or gastric acid-related diseases. The gastrointestinal inflammatory diseases or gastric acid-related diseases include peptic ulcer, gastric and duodenal ulcer, nonsteroidal anti-inflammatory drug (NSAID)-induced ulcer, *Helicobacter pylori* infection, indigestion, functional indigestion, Zollinger-Ellison syndrome, gastritis, gastroesophageal reflux disease (GERD), laryngopharyngeal reflux disease, nonerosive reflux disease (NERD), visceral referred pain, cancer, heartburn, vomiting, esophagitis, dysphagia, hypersalivation, airway obstruction, or asthma.

The imidazo[1,2-α]pyridine derivative according to the present disclosure has an excellent activity of inhibiting gastric acid secretion, and thus may be effectively used for prevention or treatment of gastrointestinal inflammatory diseases or gastric acid-related diseases, particularly peptic ulcer, gastric and duodenal ulcer, gastroesophageal reflux disease (GERD), and nonerosive reflux disease (NERD).

A pharmaceutical composition containing the compound of the present disclosure as an active ingredient may be formulated according to standard pharmaceutical practice to provide oral formulations, including powders, granules, tablets, capsules, suspensions, emulsions, syrups and aerosols, formulations for external use, suppositories, or sterile injectable formulations.

Specifically, the pharmaceutical composition of the present disclosure may be formulated using diluents or excipients, such as fillers, extenders, binders, wetting agents, disintegrants, surfactants, etc., which are commonly used. Solid formulations for oral administration include tablets, pills, powders, granules, capsules and the like, and such solid formulations may be prepared by mixing the compound with at least one or more excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, etc., can be used. For suppositories, witepsol, Macrogol, Tween 61, cacao butter, laurin fat, glycerogelatin and the like may be used, but are not limited thereto.

The preferred dose of the compound of formula 1 according to the present disclosure or a pharmaceutically acceptable salt thereof may vary depending on the patient's condition and body weight, the severity of the disease, the form of drug, and the route and period of administration, and can be suitably determined by a person skilled in the art. However, for preferred effects, the compound of the present disclosure may be administered once or several times a day at a dose of 0.0001-1000 mg/kg, preferably 0.01-500 mg/kg. Furthermore, the composition of the present disclosure may contain the compound of formula 1 in an amount of 0.0001-99 wt %, preferably 0.01-50 wt %, depending on the mode of administration.

The pharmaceutical composition of the present disclosure may further contain, in addition to the compound of formula 1 or a pharmaceutically acceptable salt thereof, one or more active ingredients exhibiting a medicinal effect equal or similar to the compound of formula 1.

Moreover, the pharmaceutical composition of the present disclosure may be administered by various routes to mammals, including rats, mice, livestock and humans. All modes of administration are contemplated, for example, administration can be orally, rectally, intravenously, intramuscularly, subcutaneously, intrathecally or by injection into cerebral blood vessels.

The present disclosure also provides the use of the imidazo[1,2-α]pyridine derivative for prevention or treatment of a disease caused by excessive secretion of gastric acid.

For preparation of medicaments, the compound represented by formula 1 may be mixed with a pharmaceutically acceptable adjuvant, diluent or carrier, and may also be combined with other active ingredients so as to exhibit synergistic effects.

The present disclosure also provides a method for preventing or treating a disease caused by excessive secretion of gastric acid, the method comprising administering an effective amount of the imidazo[1,2-α]pyridine derivative to mammals, including humans. The method for preventing or treating disease according to the present disclosure also comprises inhibiting or averting symptoms of the disease as well as addressing the disease itself prior to the onset of symptoms, by administering the compound of formula 1. The prophylactic or therapeutic dose of a particular active ingredient in the management of a disease will vary depending on the nature and severity of the disease or condition, and the route by which the active ingredient is administered.

The dose and the dose frequency will also vary according to the age, body weight, and response of the individual patient. Suitable dosing regimens can be readily selected by those skilled in the art with due consideration of such factors. In addition, the method for preventing or treating disease according to the present disclosure may further comprise administering a therapeutically effective amount of an additional active agent assisting in treatment of the disease, together with administration of the compound of formula 1. The additional active agent can exhibit a synergistic effect or an additive effect with the compound of formula 1.

The details mentioned in the pharmaceutical composition, use and treating method of the present disclosure are applied in the same manner, unless they are not contradictory to each other.

Advantageous Effects of Invention

Imidazo[1,2-α]pyridine derivatives according to the present disclosure can reversibly inhibit the proton pump, and thus can be effectively used for prevention or treatment of diseases caused by excessive secretion of gastric acid, particularly peptic ulcer, gastric and duodenal ulcer, nonsteroidal anti-inflammatory drug (NSAID)-induced ulcer, *Helicobacter pylori* infection, functional indigestion, Zollinger-Ellison syndrome, gastritis, gastroesophageal reflux disease (GERD), nonerosive reflux disease (NERD), etc.

BRIEF DESCRIPTION OF DRAWINGS

FIG. 1 is a graph showing the long-lasting inhibitory effects of compounds of the present disclosure against gastric acid secretion in lumen-perfused rats as a function of time.

MODE FOR THE INVENTION

Hereinafter, preferred examples and test examples will be presented to help understand the present disclosure. It is to be understood, however, that these examples and test examples are merely provided to facilitate understanding of the present disclosure and are not intended to limit the scope of the present disclosure.

Reference Example 1:
2-(Bromomethyl)-5-fluoro-1,3-dimethylbenzene

To 1-fluoro-3,5-dimethylbenzene (2.0 g, 16.1 mmol), p-formaldehyde (7.5 g, 250 mmol), hydrogen bromide (33 wt % in acetic acid; 35 ml) and acetic acid (12 ml, 210 mmol) were sequentially added at room temperature, followed by stirring for 5 hours. Water was added to the reaction solution to terminate the reaction, followed by extraction with diethylether. The organic layer was dried with anhydrous magnesium sulfate, and then concentrated under reduced pressure to remove the solvent. The residue was purified by column chromatography (100% hexane) to afford the title compound (1.0 g, yield: 30%) as a yellow solid.

$^1$H NMR (400 MHz, CDCl$_3$); δ 6.76 (s, 1H), 6.74 (s, 1H), 4.53 (s, 2H), 2.41 (s, 6H).

Reference Example 2:
2-(Chloromethyl)-1-methoxy-3-methylbenzene

Step 1: Synthesis of ethyl
2-methoxy-6-methylbenzoate

Ethyl 2-hydroxy-6-methylbenzoate (1.0 g, 5.6 mmol), methyl iodide (866 mg, 6.1 mmol), and potassium carbonate (1.5 g, 11.1 mmol) were dissolved in acetone, and then refluxed for 17 hours. Water was added to the reaction solution to terminate the reaction, followed by extraction with dichloromethane. The organic layer was dried with anhydrous magnesium sulfate, and then concentrated under reduced pressure to remove the solvent. The residue was purified by column chromatography (100% hexane) to afford the title compound (1.1 g, yield: 99%).

$^1$H NMR (400 MHz, CDCl$_3$); δ 7.26-7.21 (m, 1H), 6.80-6.75 (m, 2H), 4.40 (qt, J=14.4, 7.2 Hz, 2H), 3.82 (s, 3H), 2.30 (s, 3H), 1.38 (t, J=7.2 Hz, 3H).

Step 2: Synthesis of
(2-methoxy-6-methylphenyl)methanol

Anhydrous tetrahydrofuran (20 ml) was added to aluminum lithium hydride (LAH, 365 mg, 9.62 mmol) and cooled to 0° C., after which the compound (1.1 g, 5.6 mmol) prepared in step 1 was dissolved in anhydrous tetrahydrofuran (30 ml) and slowly added dropwise thereto at 0° C. The reaction solution was stirred at room temperature for 2 hours, and an aqueous solution of 15% sodium hydroxide was added thereto to terminate the reaction. Then, the reaction solution was filtered through celite and concentrated under reduced pressure, and the residue was purified by column chromatography (hexane:ethyl acetate=20:1) to afford the title compound (775 mg; yield: 91%).

$^1$H NMR (400 MHz, CDCl$_3$); δ 7.20-7.17 (m, 1H), 6.83 (m, 2H), 4.78 (s, 2H), 4.01 (s, 3H), 3.41 (s, 3H).

Step 3:
2-(Chloromethyl)-1-methoxy-3-methylbenzene

The compound (775 mg, 5.1 mmol) prepared in step 2 was dissolved in dichloromethane (30 ml), and thionyl chloride (1.0 ml, 15.2 mmol) was slowly added thereto dropwise at room temperature, followed by stirring for 2 hours. Cold ice water was added to the reaction solution to terminate the reaction, followed by extraction with dichloromethane. The organic layer was dried with anhydrous magnesium sulfate, and then concentrated under reduced pressure to remove the solvent, thereby obtaining the title compound (804 mg; yield: 93%).

$^1$H NMR (400 MHz, CDCl$_3$); δ 7.19 (t, J=8.0 Hz, 1H), 6.83 (m, 2H), 4.62 (s, 2H), 3.91 (s, 3H), 3.36 (s, 3H).

Reference Example 3:
1-Chloro-3-(chloromethyl)-2,4-dimethylbenzene

Step 1: Synthesis of 2,6-dimethyl-3-nitrobebzoic
acid

To a mixture of concentrated sulfuric acid (8 ml) and 60% nitric acid (8 ml), 2,6-dimethylbenzoic acid (3.7 g, 24.64 mmol) was added at 0° C., followed by stirring for 1.5 hours. After completion of the reaction, water was added to the reaction solution at the same temperature, followed by stirring for 0.5 hours. The produced solid was filtered under reduced pressure, washed with water, and then dried, thereby obtaining the title compound (4.7 g; yield: 98%) as a white solid.

$^1$H NMR (400 MHz, CDCl$_3$); δ 7.87 (d, J=8.0 Hz, 1H), 7.23 (d, J=7.6 Hz, 1H), 2.58 (s, 3H), 2.48 (s, 3H).

Step 2: Synthesis of methyl
2,6-dimethyl-3-nitrobenzoate

The compound (4.7 g, 24.08 mmol) prepared in step 1 was dissolved in N,N-dimethylformamide (15 ml), and potassium carbonate (6.7 g, 48.16 mmol) and methyl iodide (6.7 ml, 108.37 mmol) were sequentially added thereto, followed by stirring overnight at 0° C. The reaction was terminated by addition of cold ice water, and the reaction solution was extracted with ethyl acetate and washed with an aqueous solution of sodium chloride. The separated organic layer was dried with anhydrous sodium sulfate and concentrated under reduced pressure, and the residue was purified by column chromatography (hexane:ethyl acetate=4:1) to afford the title compound (3.8 g; yield 75%) as a yellow solid.

$^1$H NMR (400 MHz, CDCl$_3$); δ 7.84 (d, J=7.6 Hz, 1H), 7.19 (d, J=8.4 Hz, 1H), 3.96 (s, 3H), 2.46 (s, 3H), 2.36 (s, 3H).

Step 3: Synthesis of methyl 3-amino-2,6-dimethylbenzoate

The compound (3.8 g, 18.16 mmol) prepared in step 2 was dissolved in ethyl acetate (20 ml) and methanol (20 ml), and 10% palladium (760 mg, 20 wt %) was added thereto at room temperature, followed by stirring overnight in an atmosphere of hydrogen gas. After completion of the reaction, the reaction solution was filtered through celite and concentrated under reduced pressure, thereby obtaining the title compound (3 g; yield: 92%) as colorless oil.

$^1$H NMR (400 MHz, CDCl$_3$); δ 6.86 (d, J=8.0 Hz, 1H), 6.63 (d, J=8.4 Hz, 1H), 3.90 (s, 3H), 3.55 (br, 2H), 2.19 (s, 3H), 2.08 (s, 3H).

Step 4: Synthesis of methyl 3-chloro-2,6-dimethylbenzoate

To the compound (2.0 g, 11.16 mmol) prepared in step 3, water (20 ml) and concentrated hydrochloric acid (20 ml) were added, followed by stirring for 10 minutes. The reaction solution was cooled to −10° C., and a solution of sodium nitrite (810 mg, 11.72 mmol) in water (2 ml) was slowly added dropwise thereto. After 30 minutes, water (10 ml), and a solution of cuprous chloride (1.3 g, 13.39 mmol) in concentrated hydrochloric acid (10 ml) at 0° C. was slowly added dropwise to the reaction solution at −10° C., followed by stirring at the same temperature for 1 hour. Next, the reaction solution was heated at 70° C. for 1 hour. Thereafter, the reaction solution was cooled to room temperature, extracted with ethyl acetate, and washed with an aqueous solution of sodium chloride, after which the separated organic layer was dried with anhydrous sodium sulfate and concentrated under reduced pressure. The residue was purified by column chromatography (hexane:ethyl acetate=10:1) to afford the title compound (2.2 g; yield 99%) as colorless oil.

$^1$H NMR (400 MHz, CDCl$_3$); δ 7.28 (d, J=8.0 Hz, 1H), 6.98 (d, J=8.0 Hz, 1H), 3.92 (s, 3H), 2.30 (s, 3H), 2.26 (s, 3H).

Step 5: Synthesis of (3-chloro-2,6-dimethylphenyl)methanol

The compound (2.8 g, 14.35 mmol) prepared in step 4 was dissolved in tetrahydrofuran (30 ml), and lithium aluminum hydride (590 mg, 15.78 mmol) was added to the solution at −78° C., followed by stirring at room temperature for 4 hours. The reaction was terminated by addition of a 1N aqueous solution of sodium hydroxide at 0° C., and the reaction solution was stirred for 30 minutes, and then filtered through celite under reduced pressure and extracted with dichloromethane. The separated organic layer was washed with an aqueous solution of sodium chloride, dried with anhydrous sodium sulfate, and then concentrated under reduced pressure, thereby obtaining the title compound (1.9 g; yield: 79%) as a white solid.

$^1$H NMR (400 MHz, CDCl$_3$); δ 7.22 (d, J=8.0 Hz, 1H), 6.97 (d, J=8.4 Hz, 1H), 4.75 (d, J=4.8 Hz, 2H), 2.48 (s, 3H), 2.39 (s, 3H).

Step 6: Synthesis of 1-chloro-3-(chloromethyl)-2,4-dimethylbenzene

The compound (2.0 g, 11.72 mmol) prepared in step 5 was added to anhydrous dichloromethane (20 ml), and thionyl chloride (1.3 ml, 17.58 mmol) was slowly added dropwise thereto at 0° C., followed by stirring at room temperature for 3 hours. After completion of the reaction, the reaction solution was concentrated under reduced pressure to remove the solvent and an excess of thionyl chloride, and the residue was purified by column chromatography (hexane:ethyl acetate=15:1) to afford the title compound (1.8 g; yield 83%) as colorless oil.

$^1$H NMR (400 MHz, CDCl$_3$); δ 7.23 (d, J=8.0 Hz, 1H), 6.97 (d, J=8.4 Hz, 1H), 4.64 (s, 2H), 2.47 (s, 3H), 2.39 (s, 3H).

Reference Example 4: 1-Fluoro-3-(chloromethyl)-2,4-dimethylbenzene

Step 1: Synthesis of methyl 3-fluoro-2,6-dimethylbenzoate

To the compound (4.3 g, 23.99 mmol) prepared in step 3 of Reference Example 3, water (40 ml) and concentrated hydrochloric acid (40 ml) were added, and the solution was stirred for 10 minutes. The reaction solution was cooled to −10° C., and a solution of sodium nitrite (1.7 g, 11.72 mmol) in water (4 ml) was slowly added dropwise thereto. After 30 minutes, a solution of sodium fluoroborate (3.2 g, 28.79 mmol) in water (20 ml) was slowly added dropwise to the reaction solution at −10° C., followed by stirring at the same temperature for 1 hour. Next, the reaction solution was heated to room temperature and stirred for 1 hour. The produced solid was filtered under reduced pressure, washed with cold ice water and methanol, and then dried under reduced pressure, after which toluene (20 ml) was added thereto, followed by heating at 120° C. for 2 hours. The reaction solution was cooled to room temperature, and cold ice water was added thereto to terminate the reaction. Next, the reaction solution was extracted with ethyl acetate and washed with an aqueous solution of sodium chloride. The separated organic layer was dried with anhydrous sodium sulfate and concentrated under reduced pressure. The residue was purified by column chromatography (hexane:ethyl acetate=15:1) to afford the title compound (1.8 g; yield: 81%) as colorless oil.

$^1$H NMR (400 MHz, CDCl$_3$); δ 6.99 (dd, J=8.2 Hz, 5.4 Hz, 1H), 6.94 (d, J=8.0 Hz, 1H), 3.92 (s, 3H), 2.26 (s, 3H), 2.20 (d, J=2.0 Hz, 3H).

Step 2: Synthesis of 2-(chloromethyl)-4-fluoro-1,3-dimethylbenzene

The compound (1.8 g, 10.15 mmol) was reacted in the same manner as described in steps 5 and 6 of Reference Example 3, thereby obtaining the title compound (1.3 g; yield: 77%) as colorless oil.

¹H NMR (400 MHz, CDCl₃); δ 6.99 (dd, J=8.2 Hz, 5.8 Hz, 1H), 6.90 (t, J=9.0 Hz, 1H), 4.62 (s, 2H), 2.38 (s, 3H), 2.32 (d, J=2.0 Hz, 3H).

Example 1: {8-[(2,6-Dimethylbenzyl)amino]-2,3-dimethylimidazo[1,2-α]pyridin-6-yl}(3-hydroxyazetidin-1-yl)methanone Step 1: Synthesis of isopropyl 8-(2,6-dimethylbenzylamino)-2,3-dimethylimidazo[1,2-α]pyridine-6-carboxylate To isopropyl 8-amino-2,3-dimethylimidazo[1,2-α]pyridine-6-carboxylate (59 g, 18.0 mmol), anhydrous 2-propanol (590 ml) was added, and potassium carbonate (59 g, 44.9 mmol) and sodium iodide (15 g, 10.0 mmol) were sequentially added thereto. The mixture was heated to 70° C. At the same temperature, a solution of 2,6-dimethylbenzyl chloride (31 g, 20.0 mmol) in anhydrous 2-propanol (60 ml) was slowly added dropwise top the reaction mixture, followed by stirring for 4 hours. Thereafter, a solution of 2,6-dimethylbenzyl chloride (17 g, 10.8 mmol) in potassium chloride (54.7 g, 39.5 mmol) and anhydrous 2-propanol (20 ml) was added to the reaction solution, followed by stirring for 6 hours. At room temperature, the reaction was terminated by addition of water, and the reaction solution was stirred for 30 minutes. The produced solid was filtered, washed sequentially with water and cold 2-propanol, and then dried, thereby obtaining the title compound (55 g; yield: 88%) as a white solid.

¹H NMR (400 MHz, CDCl₃); δ 8.25 (s, 1H), 7.30 (s, 1H), 7.15-7.09 (m, 1H), 7.06-7.04 (m, 2H), 6.73 (s, 1H), 5.31-5.26 (m, 1H), 4.84 (br, 1H), 4.41 (d, J=4.4 Hz, 2H), 2.39 (s, 12H), 1.40 (d, J=6.4 Hz, 6H).

Step 2: Synthesis of 8-(2,6-dimethylbenzylamino)-2,3-dimethylimidazo[1,2-α]pyridine-6-carboxylic acid The compound (92.5 g, 25.3 mmol) prepared in step 1 was dissolved in ethanol (920 ml), and a 2N aqueous solution of sodium hydroxide (500 ml) was added to the solution at room temperature, followed by stirring at 80° C. for 2 hours. The reaction solution was cooled to room temperature and concentrated under reduced pressure the solvent, after which water was added to the residue and a 2N aqueous solution of hydrochloric acid (500 ml) was slowly added dropwise to the aqueous solution at 0° C. to adjust the pH to about 5. Next, the solution was stirred for 8 hours, filtered, washed with water, and then dried, thereby obtaining the title compound (69 g; yield 85%) as a white solid.

¹H NMR (400 MHz, CDCl₃+CD₃OD); δ 8.36 (s, 1H), 7.32 (s, 1H), 7.16-7.14 (m, 1H), 7.11-7.10 (m, 2H), 4.50 (s, 2H), 2.52 (s, 3H), 2.42 (s, 9H).

Step 3: Synthesis of {8-[(2,6-dimethylbenzyl)amino]-2,3-dimethylimidazo[1,2-α]pyridin-6-yl}(3-hydroxyazetidin-1-yl)methanone The compound (30 mg, 0.06 mmol) prepared in step 2 was dissolved in anhydrous dichloromethane (5 ml). Then, 1-ethyl-3-(3-dimethylaminopropyl)-carbodiimide chloride (EDCI, 18 mg, 0.09 mmol), 1-hydroxy-benzotriazole hydrate (HOBt, 13 mg, 0.09 mmol), 3-hydroxyazetidine (8.1 mg, 0.07 mmol) and triethylamine (34 μl, 0.25 mmol) were sequentially added to the solution at 0° C., followed by stirring at room temperature for 22 hours. Next, an aqueous solution of sodium bicarbonate was slowly added to the reaction solution at 0° C. to terminate the reaction, and the reaction solution was extracted with dichloromethane. The separated organic layer was washed with a saturated aqueous solution of sodium chloride, dried with anhydrous sodium sulfate, and then concentrated under reduced pressure. The residue was purified by column chromatography (hexane:ethyl acetate=3:1) to afford the title compound (35 mg; yield: 95%) as a white solid.

¹H NMR (400 MHz, CDCl₃); δ 7.62 (s, 1H), 7.14-7.10 (m, 1H), 7.05-7.03 (m, 2H), 6.39 (s, 1H), 4.92 (br, 1H), 4.77-4.71 (m, 1H), 4.53-4.49 (m, 2H), 4.14 (d, J=6.8, 2H), 4.15-4.13 (m, 2H), 2.38-2.34 (m, 12H).

Based on the reaction procedure described in Example 1, compounds of Examples 2 to 48, which have different substituents as shown in Table 1 below, were synthesized.

| Example | Chemical structure | Yield | NMR spectrum data |
|---|---|---|---|
| 2 | 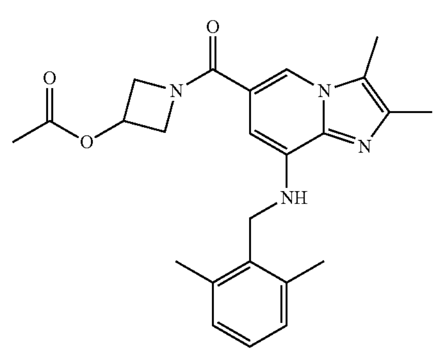 [SMILES: CC(=O)OC1CN(C(=O)c2cc(NCc3c(C)cccc3C)c3nc(C)c(C)n3c2)C1] | 79% | ¹H NMR (400 MHz, CDCl₃); δ 7.64 (S, 1H), 7.15-7.11 (m, 1H), 7.06-7.04 (m, 2H), 6.37 (s, 1H), 5.30-5.27 (m, 1H), 4.80-4.95 (m, 1H), 4.70-4.50 (m, 2H), 4.37 (d, J = 4.0 Hz, 2H), 4.30-4.20 (m, 2H), 2.38-2.34 (m, 12H), 2.13 (s, 3H) |

-continued
| Example | Chemical structure | Yield | NMR spectrum data |
|---|---|---|---|
| 3 | 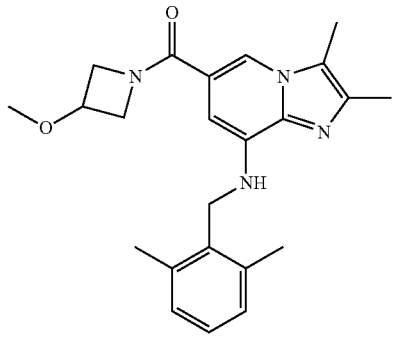 | 26% | ¹H NMR (400 MHz, CDCl₃); δ 7.63 (s, 1H), 7.14-7.10 (m, 1H), 7.05-7.03 (m, 2H), 6.39 (s, 1H), 4.91 (m, 1H), 4.45 (br, 2H), 4.37 (d, J = 4.0 Hz, 2H), 4.30-4.27 (m, 1H), 4.17 (br, 2H), 3.34 (s, 3H), 2.37-2.34 (m, 12H) |
| 4 | 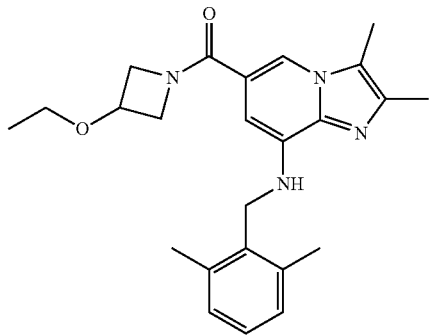 [SMILES: CCOC1CN(C(=O)c2cc(NCc3c(C)cccc3C)c3nc(C)c(C)n3c2)C1] | 26% | ¹H NMR (400 MHz, CDCl₃); δ 7.63 (s, 1H), 7.14-7.09 (m, 1H), 7.05-7.01 (m, 2H), 6.39 (s, 1H), 4.86 (br, 1H), 4.56 (br, 2H), 4.37 (d, J = 5.6 Hz, 2H), 4.15-4.12 (m, 2H), 3.50-3.48 (qt, 2H), 2.37-2.29 (m, 12H), 1.26 (t, J = 7.0 Hz, 3H) |
| 5 | 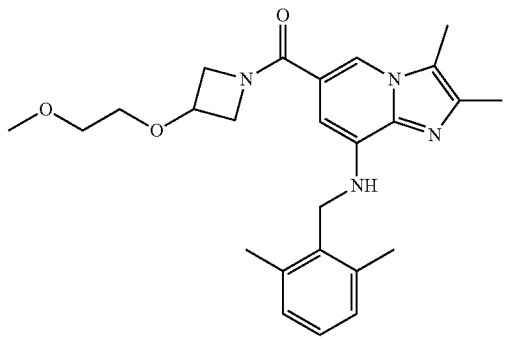 | 35% | ¹H NMR (400 MHz, CDCl₃); δ 7.62 (s, 1H), 7.14-7.11 (m, 1H), 7.08-7.03 (m, 2H), 6.39 (s, 1H), 4.86 (m, 1H), 4.45-4.36 (m, 7H), 3.60-3.57 (m, 4H), 3.40 (s, 3H), 2.37-2.34 (m, 12H) |
| 6 | 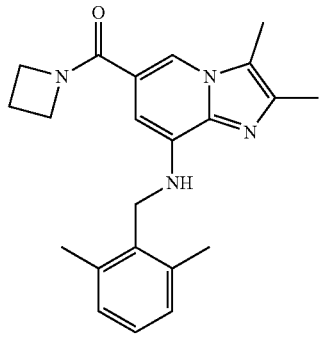 [SMILES: Cc1cccc(C)c1CNc1cc(C(=O)N2CCC2)cn2c(C)c(C)nc12] | 85% | ¹H NMR (400 MHz, CDCl₃); δ 7.63 (d, J = 1.2 Hz, 1H) 7.13 (dd, J = 8.4, 6.8 Hz, 1H) 7.06-7.04 (m, 2H) 6.42 (d, J = 1.2 Hz, 1H), 4.86-4.84 (m, 1H), 4.41-4.28 (m, 4H), 4.37 (d, J = 4.4 Hz, 2H), 3.75-3.69 (m, 1H), 2.43-2.34 (m, 13H) |

-continued
| Example | Chemical structure | Yield | NMR spectrum data |
|---|---|---|---|
| 7 | 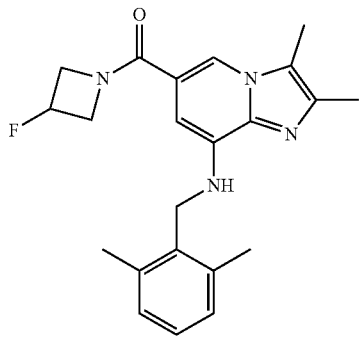 [SMILES: Cc1cccc(C)c1CNc1cc(C(=O)N2CC(F)C2)cn2c(C)c(C)nc12] | 59% | $^1$H NMR (400 MHz, CDCl$_3$); δ 7.63 (s, 1H), 7.14-7.10 (m, 1H), 7.05-7.03 (m, 2H), 6.36 (s, 1H), 5.48-5.45 (m, 0.5H), 5.33-5.29 (m, 0.5H), 4.90 (br, 1H), 4.58-4.36 (m, 6H), 2.37-2.34 (m, 12H) |
| 8 | 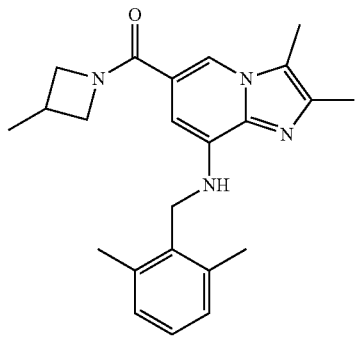 | 84% | $^1$H NMR (400 MHz, CDCl$_3$); δ 7.63 (d, J = 1.2 Hz, 1H), 7.13 (dd, J = 8.4, 6.8 Hz, 1H), 7.06-7.04 (m, 2H), 6.42 (d, J = 1.6 Hz, 1H), 4.90-4.88 (m, 1H), 4.51 (br, 2H), 4.38 (d, J = 4.0 Hz, 2H 3.95-3.82 (m, 1H), 2.87-2.79 (m, 1H), 2.38-2.34 (m, 12H), 1.32 (d, J = 6.8 Hz, 1H) |
| 9 | 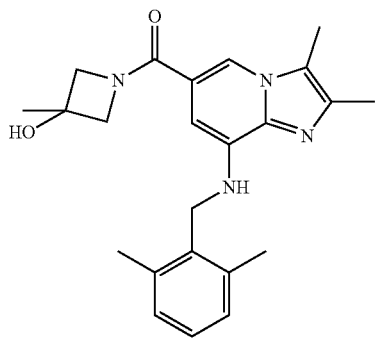 | 72% | $^1$H NMR (400 MHz, CDCl$_3$); δ 7.60 (s, 1H), 7.14-7.10 (m, 1H), 7.05-7.03 (m, 1H), 6.41 (m, 1H), 5.08 (br, 1H), 4.35 (d, J = 4.0 Hz, 2H) 4.15-4.12 (m, 4H), 2.38-2.33 (m, 12H), 2.05 (s, 3H) |
| 10 | 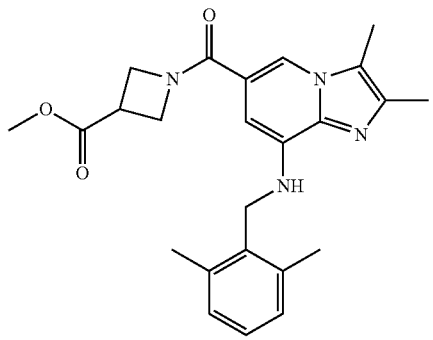 | 85% | $^1$H NMR (400 MHz, CDCl$_3$); δ 7.64 (d, J = 1.6 Hz, 1H) 7.13-7.11 (m, 1H), 7.06-7.04 (m, 2H), 6.38 (S, 1H), 4.83-4.86 (m, 1H), 4.62-4.40 (m, 4H), 4.37 (d, J = 4.4 Hz, 2H), 3.80 (s, 3H), 3.60-3.50 (m, 1H), 2.38-2.34 (m, 12H) |

| Example | Chemical structure | Yield | NMR spectrum data |
|---|---|---|---|
| 11 | 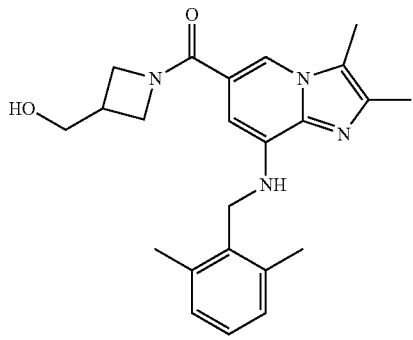 [SMILES: Cc1cccc(C)c1CNc1cc(C(=O)N2CC(CO)C2)cn2c(C)c(C)nc12] | 79% | ¹H NMR (400 MHz, CDCl₃); δ 7.64 (d, J = 1.6, 1H), 7.64 (dd, J = 8.8, 6.8 Hz, 1H), 7.06-7.04 (H, 2H), 6.43 (S, 1H), 4.92 (br, 1H), 4.44-4.01 (m, 4H), 4.37 (d, J = 4.4 Hz, 2H), 3.84 (d, J = 5.6 Hz, 2H), 2.87-2.82 (m, 1H), 2.38-2.36 (m, 12H) |
| 12 | 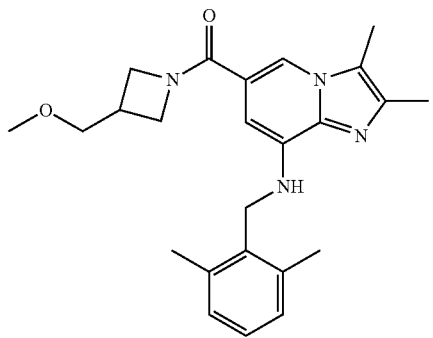 | 99% | ¹H NMR (400 MHz, CDCl₃); δ 7.65 (d, J = 1.6 Hz), 7.15-7.11 (m, 1H), 7.06-7.04 (m, 1H), 6.42 (s, 1H), 4.85 (br, 1H), 4.47-3.99 (m, 1H), 4.37 (d, J = 4.4 Hz, 2H), 3.59 (d, J = 6.4 Hz, 2H), 3.0-2.92 (m, 1H), 2.38-2.34 (m, 12H), 2.18 (s, 3H) |
| 13 | 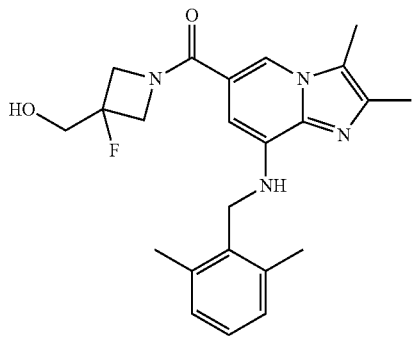 [SMILES: Cc1cccc(C)c1CNc1cc(C(=O)N2CC(F)(CO)C2)cn2c(C)c(C)nc12] | 53% | ¹H NMR (400 MHz, CDCl₃); δ 7.65 (s, 1H), 7.14-7.11 (m, 1H), 7.05-7.04 (m, 2H), 6.37 (s, 1H), 4.91 (br, 1H), 4.41-4.37 (m, 6H), 3.93 (d, J = 20.8, 2H), 2.38-2.34 (m, 12H) |
| 14 | 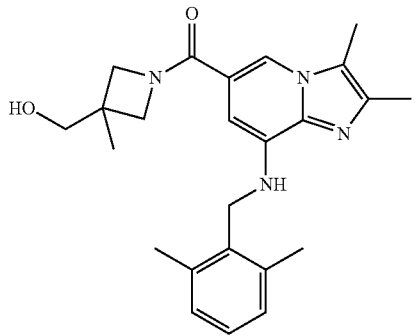 [SMILES: Cc1cccc(C)c1CNc1cc(C(=O)N2CC(C)(CO)C2)cn2c(C)c(C)nc12] | 57% | ¹H NMR (400 MHz, CDCl₃); δ 7.64 (s, 1H), 7.11 (dd, J = 8.0, 6.4 Hz, 1H), 7.03 (m, 2H), 6.43 (s, 1H), 4.93-4.91 (m, 1H), 4.36 (d, J = 4.4 Hz, 2H), 4.29-3.85 (m, 4H), 3.47 (d, J = 0.8 Hz, 2H), 2.37 (s, 6H), 2.34 (d, J = 7.6 Hz, 6H), 1.32 (S, 3H) |

| Example | Chemical structure | Yield | NMR spectrum data |
|---|---|---|---|
| 15 | 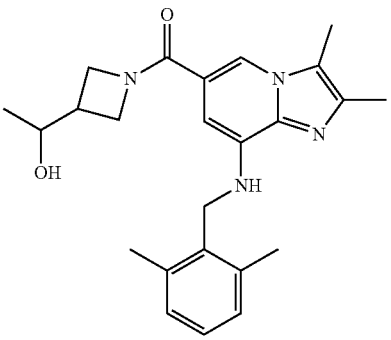 [SMILES: Cc1cccc(C)c1CNc1cc(C(=O)N2CC(C(C)O)C2)cn2c(C)c(C)nc12] | 76% | $^1$H NMR (400 MHz, CDCl$_3$); δ 7.64 (d, J = 1.2 Hz, 1H), 7.13 (dd, J = 8.8, 6.8 Hz, 1H), 7.05-7.04 (S, 1H), 6.42 (s, 1H), 4.87-4.86 (m, 1H), 4.67 (d, J = 4.4 Hz, 2H), 4.36-4.01 (m, 4H), 2.68 (m, 1H), 2.38-2.34 (m, 12H), 1.21 (d, J = 6.4 Hz, 3H) |
| 16 | 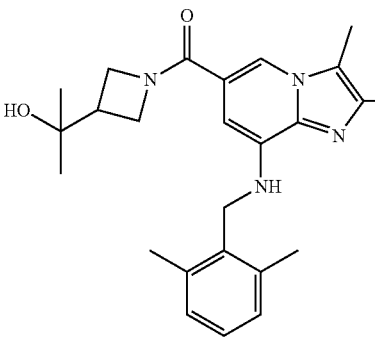 | 34% | $^1$NMR (400 MHz, CDCl$_3$); δ 7.63 (d, J = 1.2 Hz, 1H), 7.11 (dd, J = 6.8, 6.4 Hz, 1H), 7.04-7.03 (m, 2H), 6.42 (s, 1H), 4.90 (br, 1H), 4.37 (d, J = 1.1 Hz, 2H), 4.31-4.11 (m, 4H), 2.701 (m, 1H), 2.37-2.33 (m, 12H), 1.21 (s, 6H) |
| 17 | 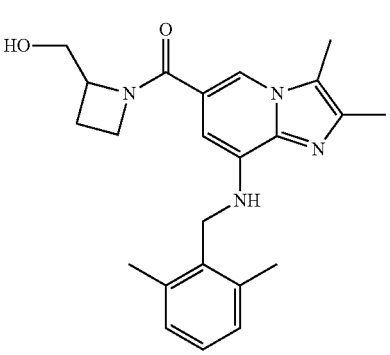 [SMILES: Cc1cccc(C)c1CNc1cc(C(=O)N2CCC2CO)cn2c(C)c(C)nc12] | 48% | $^1$H NMR (400 MHz, CDCl$_3$); δ 7.65 (s, 1H), 7.13 (dd, J = 8.4, 6.8 Hz, 1H), 7.06-7.04 (m, 2H), 6.41 (S, 1H), 4.93-4.83 (m, 3H), 4.38-4.30 (m, 4H), 3.97-3.92 (m, 1H), 3.83-3.81 (m, 1H), 2.44-2.35 (m, 13H), 2.14-2.06 (m, 1H) |
| 18 | 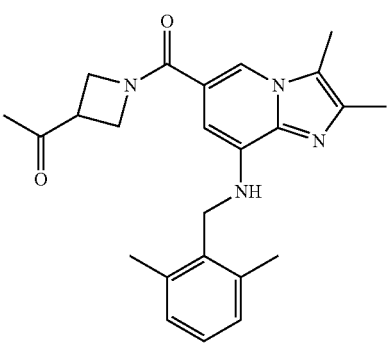 [SMILES: CC(=O)C1CN(C(=O)c2cc(NCc3c(C)cccc3C)c3nc(C)c(C)n3c2)C1] | 68% | $^1$H NMR (400 MHz, CDCl$_3$); 7.64 (d, J = 1.2 Hz, 1H), 7.15-7.11 (m, 1H), 7.06-7.04 (m, 2H), 6.39 (m, 2H), 4.92-4.89 (m, 1H), 4.60 (br, 1H), 4.46-4.37 (m, 4H), 4.28 (br, 1H), 3.67-3.58 (m, 1H), 2.38-2.34 (m, 12H), 2.25 (S, 3H) |

-continued
| Example | Chemical structure | Yield | NMR spectrum data |
|---|---|---|---|
| 19 | 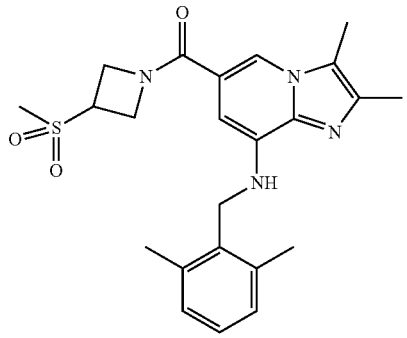 [SMILES: Cc1cccc(C)c1CNc1cc(C(=O)N2CC(S(C)(=O)=O)C2)cn2c(C)c(C)nc12] | 74% | $^1$H NMR (400 MHz, CDCl$_3$); δ 7.64 (s, 1H), 7.15-7.11 (m, 1H), 7.06-7.04 (m, 2H), 6.33 (sm 1H), 4.93 (br, 1H), 4.62-4.54 (m, 4H), 4.37 (d, J = Hz, 2H), 4.12-4.05 (m, 1H), 2.95 (s, 3H), 2.38-2.34 (m, 12H) |
| 20 | 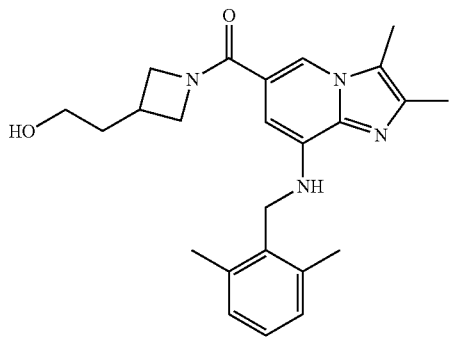 [SMILES: Cc1cccc(C)c1CNc1cc(C(=O)N2CC(CCO)C2)cn2c(C)c(C)nc12] | 40% | $^1$H NMR (400 MHz, CDCl$_3$); δ 7.63 (d, J = 0.8 Hz, 1H), 7.12 (dd, J = 8.4, 6.8 Hz, 1H), 7.05-7.03 (m, 2H), 6.42 (s, 1H), 4.91-4.90 (m, 1H), 4.49-4.31 (m, 4H), 4.15-4.09 (m, 2H), 4.04-3.91 (m, 2H), 3.67 (t, J = 5.8 Hz, 3H), 2.89-2.82 (m, 1H), 2.38-2.34 (m, 12H) |
| 21 | 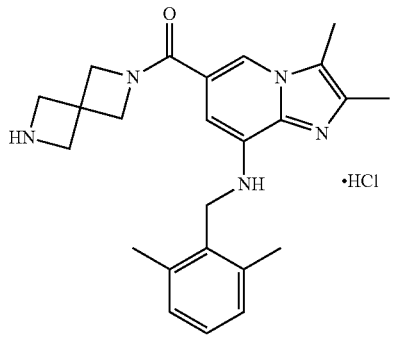 [SMILES: Cc1cccc(C)c1CNc1cc(C(=O)N2CC3(CNC3)C2)cn2c(C)c(C)nc12 ; Cl] | 67% | $^1$H NMR (400 MHz, CD3OD); δ 8.56 (s, 1H), 7.20-7.09 (m, 4H), 4.57-.316 (m, 12H), 2.64-2.42 (m, 12H) |
| 22 | 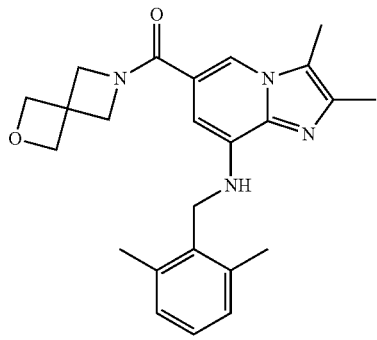 [SMILES: Cc1cccc(C)c1CNc1cc(C(=O)N2CC3(COC3)C2)cn2c(C)c(C)nc12] | 98% | $^1$H NMR (400 MHz, CDCl$_3$); δ 7.62 (s, 1H), 7.15-7.11 (m, 1H), 7.06-7.04 (m, 2H), 6.36 (s, 1H), 4.93 (m, 1H), 4.85 (br, 4H), 4.46 (br, 4H), 4.37 (d, J = 4.4, 2H), 2.38-2.35 (m, 12H) |

| Example | Chemical structure | Yield | NMR spectrum data |
|---|---|---|---|
| 23 | 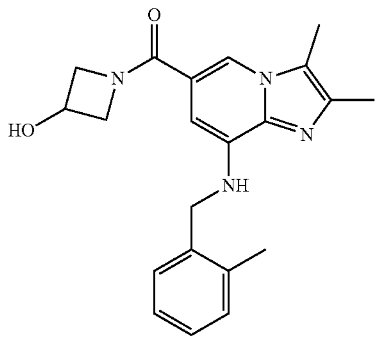 [SMILES: Cc1ccccc1CNc1cc(C(=O)N2CC(O)C2)cn2c(C)c(C)nc12] | 82% | ¹H NMR (400 MHz, CDCl3); δ 7.66 (s, 1H), 7.32 (d, J = 7.2 Hz, 1H), 7.19 (d, J = 4.0 Hz, 2H), 7.16-7.14 (m, 1H), 6.14 (s, 1H), 5.46 (br, 1H), 4.69-4.63 (m, 1H), 4.44-4.22 (m, 4H), 3.99-3.98 (m, 2H), 2.38-2.37 (m, 9H) |
| 24 | 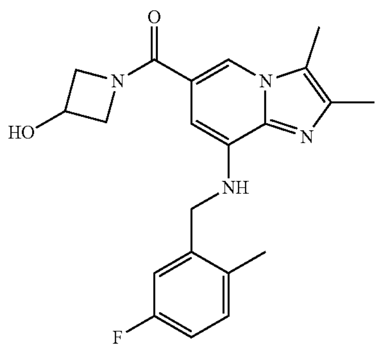 [SMILES: Cc1ccc(F)cc1CNc1cc(C(=O)N2CC(O)C2)cn2c(C)c(C)nc12] | 38% | ¹H NMR (400 MHz, CDCl$_3$); δ 7.67 (d, J = 1.6 Hz, 1H), 7.15 (br, 1H), 7.09-7.08 (m, 1H), 7.02-7.00 (m, 1H), 6.15 (S, 1H), 5.35 (m, 1H), 4.72-4.62 (m, 1H), 4.40-4.38 (m, 4H), 4.02-4.00 (m, 2H), 2.39-2.26 (m, 9H) |
| 25 | 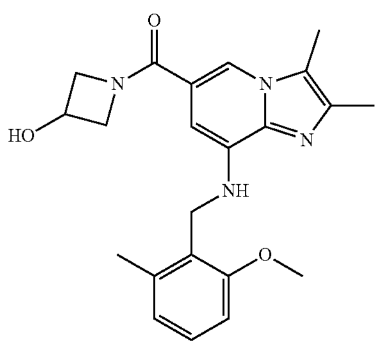 [SMILES: COc1cccc(C)c1CNc1cc(C(=O)N2CC(O)C2)cn2c(C)c(C)nc12] | 81% | ¹H NMR (400 MHz, CDCl$_3$); δ 7.61 (d, J = 1.6 Hz, 1H), 7.19 (t, J = 8.0, 7.6 Hz, 1H), 6.82, (d, J = 7.6 Hz, 1H), 6.79 (d, J = 8 Hz, 2H), 6.46 (d, J = 1.2 Hz, 1H), 4.69-4.63 (m, 1H), 4.52-4.60 (m, 4H), 4.25 (br, 1H), 4.02 (br, 1H), 3.84 (S, 3H), 3.38-3.36 (m, 1H), 2.41 (S, 3H), 2.37 (S, 3H), 2.33 (S, 3H) |
| 26 | 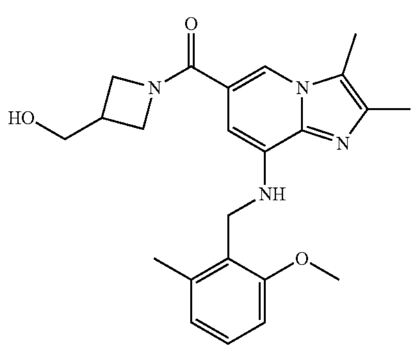 [SMILES: COc1cccc(C)c1CNc1cc(C(=O)N2CC(CO)C2)cn2c(C)c(C)nc12] | 43% | ¹H NMR (400 MHz, CDCl$_3$); δ 7.62 (d, J = 1.2 Hz, 1H), 7.17 (t, J = 8.4, 7.6 Hz, 1H), 6.80 (d, J = 8.0 Hz, 2H), 6.75 (d, J = Hz, 2H), 6.44 (S, 1H), 5.08-5.07 (m, 1H), 4.43-4.42 (m, 3H), 4.26-4.09 (m, 2H), 3.97 (br, 1H), 3.81 (S, 2H), 3.80 (S, 3H), 2.38-2.34 (m, 9H) |

| Example | Chemical structure | Yield | NMR spectrum data |
|---|---|---|---|
| 27 | 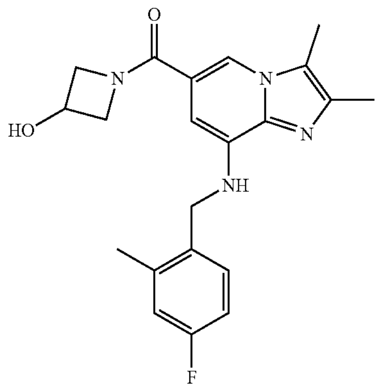 [SMILES: Cc1cc(F)ccc1CNc1cc(C(=O)N2CC(O)C2)cn2c(C)c(C)nc12] | 72% | ¹H NMR (400 MHz, CD₃OD); δ 7.78 (s, 1H), 7.33 (dd, J = 8.0 Hz, 6.0 Hz, 1H), 6.98-6.96 (m, 1H), 6.89-6.85 (M, 1H), 6.28 (s, 1H), 4.62 (s, 2H), 4.32-4.28 (m, 1H), 4.20-4.16 (m, 1H), 4.00 (m, 1H), 3.92 (m, 1H), 2.81 (m, 1H), 2.41 (s, 6H), 2.35 (s, 3H) |
| 28 | 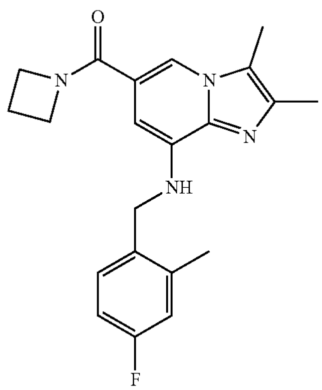 [SMILES: Cc1cc(F)ccc1CNc1cc(C(=O)N2CCC2)cn2c(C)c(C)nc12] | 77% | ¹H NMR (400 MHz, CDCl₃); δ 7.67 (d, J = 1.6, 1H), 7.29-7.28 (m, 1H), 6.93-6.90 (m, 1H), 6.85-6.80 (m, 1H), 6.19 (s, 1H), δ 4.40 (d, J = 5.6 Hz, 2H), 4.19 (br, 4H), 2.40-2.28 (m, 14H) |
| 29 | 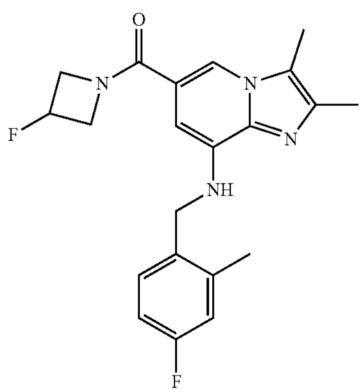 [SMILES: Cc1cc(F)ccc1CNc1cc(C(=O)N2CC(F)C2)cn2c(C)c(C)nc12] | 85% | ¹H NMR (400 MHz, CDCl₃); δ 7.67 (S, 1H), 7.30-7.27 (m, 1H), 6.94-6.91 (m, 1H), 6.86-6.82 (m, 1H), 6.12 (S, 1H), 5.41-5.38 (m, 1H), 5.27-5.24 (m, 1H), 4.400-4.22 (m, 6H), 2.39-2.38 (m, 9H) |
| 30 | 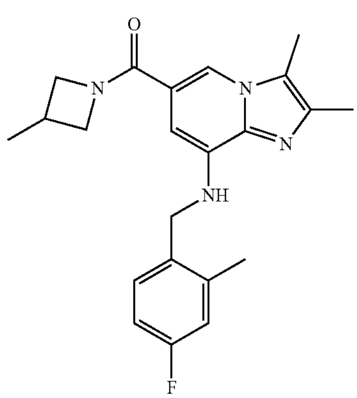 | 71% | ¹H NMR (MHz, CDCl₃); δ 7.67 (d, J = 2.4 Hz, 1H), 7.30-7.27 (m, 1H), 6.93-6.90 (m, 1H), 6.85-6.81 (m, 1H), 6.16 (d, J = 1.2 Hz, 1H), 5.33-5.31 (m, 1H), 4.39 (d, J = 5.2, 1H), 4.27 (br, 2H), 3.86-3.68 (m, 2H), 2.76-7.71 (m, 1H), 2.38 (S, 9H), 1.26 (d, J = 6.8 Hz, 3H) |

| Example | Chemical structure | Yield | NMR spectrum data |
|---|---|---|---|
| 31 | 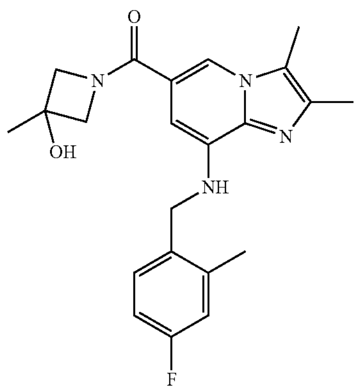 | 68% | ¹H NMR (400 MHz, CDCl₃); δ 7.66 (S, 1H), 7.30-7.26 (m, 1H), 6.93-6.90 (m, 1H), 6.86-6.81 (m, 1H), 6.14 (S, 1H), 5.38-5.36 (m, 1H), 4.38 (d, J = 4.8 Hz, 2H), 4.10-3.90 (m, 4H), 2.38 (S, 9H), 1.53 (S, 3H) |
| 32 | 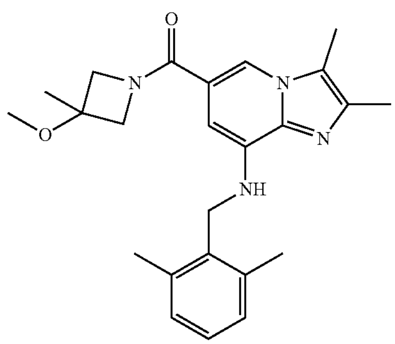 | 81% | ¹H NMR (400 MHz, CDCl₃); δ 7.64 (S, 1H), 7.12 (dd, J = 8.4, 7.2 Hz, 1H), 7.05-7.03 (m, 2H), 6.40 (S, 1H), 4.87 (br, 1H), 4.38-4.37 (m, 2H), 4.30-4.06 (m, 4H), 3.29 (s, 3H), 2.38-2.34 (m, 12H), 1.54 (S, 3H) |
| 33 | 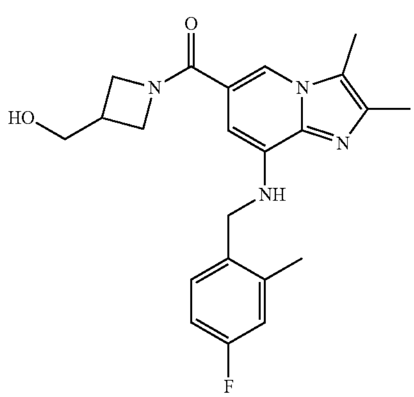 [SMILES: Cc1cc(F)ccc1CNc1cc(C(=O)N2CC(CO)C2)cn2c(C)c(C)nc12] | 80% | ¹H NMR (400 MHz, CDCl₃); δ 7.67 (d, J = 1.6 Hz, 1H), 7.30-7.27 (m, 1H), 6.93-6.90 (m, 1H), 6.86-6.81 (m, 1H), 6.17 (d, J = 1.2, 1H), 5.35-5.31 (m, 1H), 4.39 (d, J = 5.2, 2H), 4.22 (br, 2H), 3.96-3.92 (m, 2H), 3.81-3.80 (m, 2H), 2.85-2.82 (m, 1H), 2.38 (S, 9H) |
| 34 | 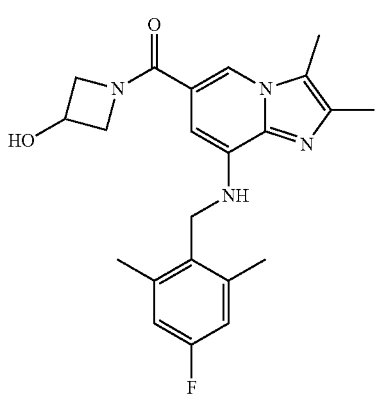 [SMILES: Cc1cc(F)cc(C)c1CNc1cc(C(=O)N2CC(O)C2)cn2c(C)c(C)nc12] | 43% | ¹H NMR (400 MHz, CDCl₃); δ 7.62 (d, J = 1.2 Hz, 1H), 6.76 (d, J = 9.6, 2H), 6.40 (d, J = 1.2 Hz, 1H), 4.86 (br, 1H), 4.78-4.73 (m, 1H), 4.54-4.53 (m, 2H), 4.31 (d, J = 4.4 Hz, 2H), 4.16 (br, 2H), 2.37-2.35 (m, 12H) |

-continued

| Example | Chemical structure | Yield | NMR spectrum data |
|---|---|---|---|
| 35 | 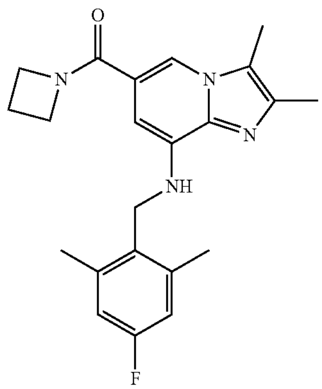 [SMILES: Cc1cc(F)cc(C)c1CNc1cc(C(=O)N2CCC2)cn2c(C)c(C)nc12] | 95% | $^1$H NMR (400 MHz, CDCl$_3$); δ 7.63 (s, 1H), 6.76 (d, J = 9.6 Hz, 2H), 6.42 (s, 1H), 4.79 (br, 1H), 4.41-4.27 (m, 4H), 4.32 (d, J = 4.4 Hz), 2.43-2.35 (m, 14H) |
| 36 | 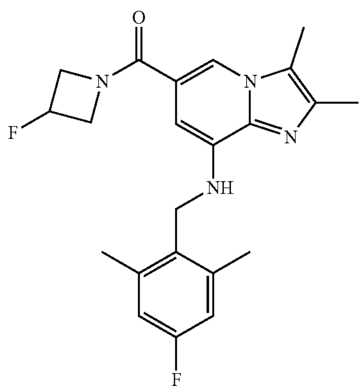 [SMILES: Cc1cc(F)cc(C)c1CNc1cc(C(=O)N2CC(F)C2)cn2c(C)c(C)nc12] | 83% | $^1$H NMR (400 MHz, CDCl$_3$); δ 7.64 (s, 1H), 6.77 (d, J = 9.6, 2H), 6.37 (sm 1H), 5.50-5.45 (m, 0.5H), 5.36-5.30 (m, 0.5H), 4.85 (br, 1H), 4.63-4.41 (m, 4H), 4.32 (d, J = 4.0 Hz, 2H), 2.38-2.35 (m, 12H) |
| 37 | 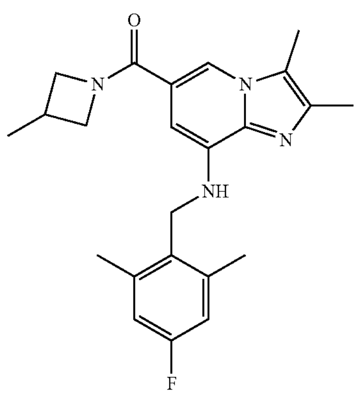 | 76% | $^1$H NMR (400 MHz, CDCl$_3$); δ 7.64 (d, J = 1.6 Hz, 1H), 6.76 (d, J = 9.6 Hz, 2H), 6.42 (d, J = 1.2 Hz, 1H), 4.80 (br, 1H), 4.51-4.32 (m, 4H), 3.97-3.83 (m, 2H), 2.87-2.80 (m, 1H), 2.38-2.35 (m, 12H), 1.32 (d, J = 7.2 Hz, 3H) |
| 38 | 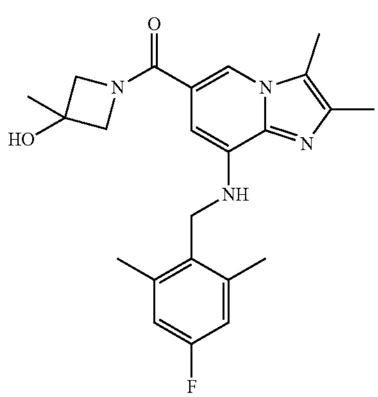 [SMILES: Cc1cc(F)cc(C)c1CNc1cc(C(=O)N2CC(C)(O)C2)cn2c(C)c(C)nc12] | 84% | $^1$H NMR (400 MHz, CDCl$_3$); δ 7.61 (s, 1H), 6.75 (d, J = 9.6, 2H), 6.40 (s, 1H), 4.94 (br, 1H), 4.30 (d, J = 4.0 Hz, 2H), 4.19-4.09 (m, 4H), 2.36-2.34 (m, 12H), 1.55 (s, 3H) |

| Example | Chemical structure | Yield | NMR spectrum data |
|---|---|---|---|
| 39 | 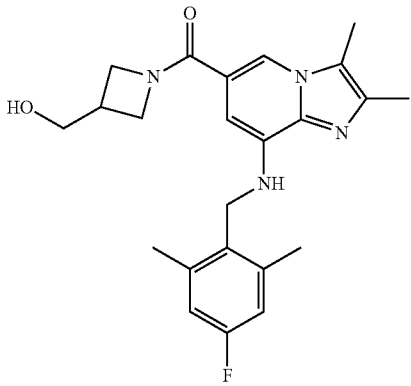 [SMILES: Cc1cc(F)cc(C)c1CNc1cc(C(=O)N2CC(CO)C2)cn2c(C)c(C)nc12] | 80% | $^1$H NMR (400 MHz, CDCl$_3$); δ 7.64 (d, J = 1.2 Hz, 1H), 6.76 (d, J = 10 Hz, 2H), 6.42 (d, J = 1.2 Hz, 1H), 4.83 (br, 1H), 4.53-4.01 (m, 4H), 4.32 (d, J = 4.4 Hz, 2H), 3.86 (d, J = 6.4 Hz, 2H), 2.92-2.88 (m, 1H), 2.37-2.35 (m, 12H) |
| 40 | 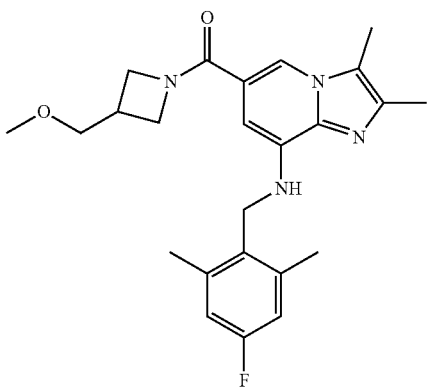 | 61% | $^1$H NMR (400 MHz, CDCl$_3$); δ 7.65 (S, 1H), 6.76 (d, J = 9.6, 2H), 6.42 (S, 1H), 4.80 (m, 1H), 4.45-3.99 (m, 6H), 3.58 (d, J = 6.4, 2H), 3.40 (S, 3H), 2.97-2.94 (m, 1H), 2.37-2.34 (m, 12H) |
| 41 | 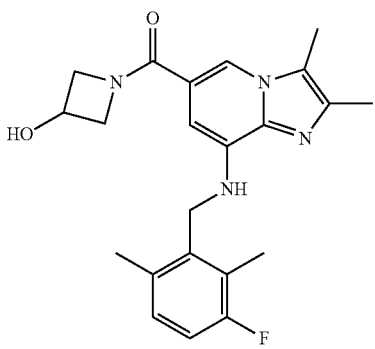 [SMILES: Cc1ccc(F)c(C)c1CNc1cc(C(=O)N2CC(O)C2)cn2c(C)c(C)nc12] | 50% | $^1$H NMR (400 MHz, CDCl$_3$); δ 7.64 (S, 1H), 7.05-7.02 (m, 1H), 6.95-6.90 (m, 1H), 6.42 (S, 1H), 4.68-4.66 (m, 1H), 4.53-4.06 (m, 7H), 2.41-2.29 (m, 14H) |
| 42 | 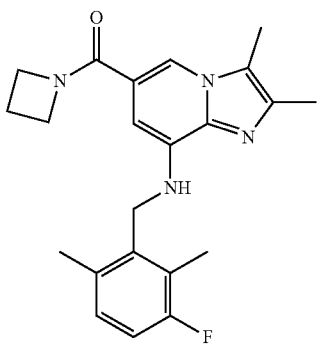 [SMILES: Cc1ccc(F)c(C)c1CNc1cc(C(=O)N2CCC2)cn2c(C)c(C)nc12] | 99% | $^1$H NMR (400 MHz, CDCl$_3$); δ 7.64 (d, J = 1.6 Hz, 1H), 7.02-6.98 (m, 1H), 6.94-6.89 (m, 1H), 6.44 (s, 1H), 4.89 (br, 1H), 4.37-4.29 (m, 6H), 2.42-2.27 (m, 14H) |

| Example | Chemical structure | Yield | NMR spectrum data |
| --- | --- | --- | --- |
| 43 | 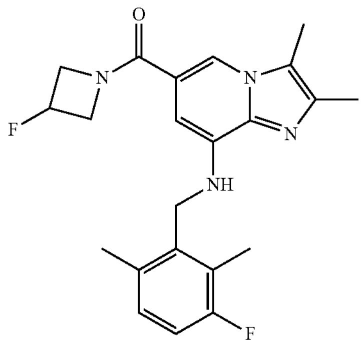 [SMILES: Cc1ccc(F)c(C)c1CNc1cc(C(=O)N2CC(F)C2)cn2c(C)c(C)nc12] | 73% | ¹H NMR (400 MHz, CDCl3); δ 7.64 (d, J = 1.2 Hz, 1H), 7.02-6.99 (m, 1H), 6.94-6.90 (m, 1H), 6.38 (d, J = 1.2 Hz, 1H), 5.50-5.45 (m, 0.5H), 5.36-5.31 (m, 0.5H), 4.82-4.87 (m, 1H), 4.60-4.53 (m, 2H), 4.53-4.35(m, 5H), 2.38-2.27 (m, 12H) |
| 44 | 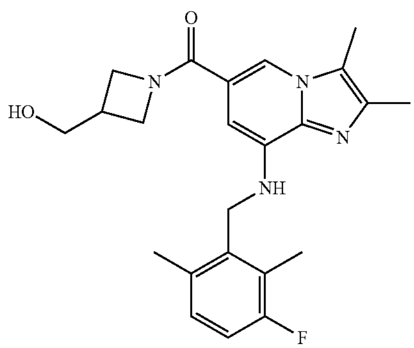 [SMILES: Cc1ccc(F)c(C)c1CNc1cc(C(=O)N2CC(CO)C2)cn2c(C)c(C)nc12] | 73% | ¹H NMR (400 MHz, CDCl$_3$); δ 7.65 (d, J = 1.6 Hz, 1H), 7.02-6.98 (m, 1H), 6.93-6.89 (m, 1H), 6.43 (d, J = 0.8 Hz, 1H), 4.87 (br, 1H), 4.44-4.00 (m, 4H), 4.35 (d, J = 4.4, 2H), 3.86-3.85 (d, J = 5.6, 2H), 2.95-2.85 (m, 1H), 2.37-2.33 (m, 9H), 2.27 (d, J = 2.0 Hz, 3H) |
| 45 | 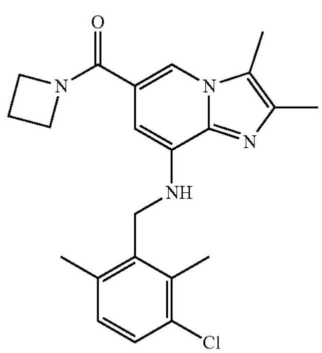 [SMILES: Cc1ccc(Cl)c(C)c1CNc1cc(C(=O)N2CCC2)cn2c(C)c(C)nc12] | 73% | ¹H NMR (400 MHz, CDCl$_3$); δ 7.64 (d, J = 1.2 Hz, 1H), 7.25 (d, J = 8.0 Hz, 1H), 6.99 (d, J = 8.4 Hz, 1H), 6.43 (d, J = 1.2 Hz, 1H), 4.83-4.81 (m, 1H), 4.39-4.28 (m, 4H), 4.38 (d, J = 4.4 Hz, 2H), 2.44-2.35 (m, 14H) |
| 46 | 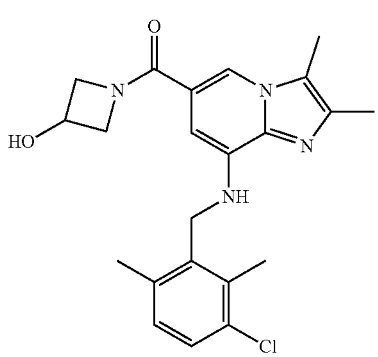 [SMILES: Cc1ccc(Cl)c(C)c1CNc1cc(C(=O)N2CC(O)C2)cn2c(C)c(C)nc12] | 84% | ¹H NMR (400 MHz, CDCl$_3$); δ 7.64 (S, 1H), 7.27-7.23 (m, 1H), 7.00-6.98 (m, 1H), 6.40 (S, 1H), 4.92-4.86 (m, 1H), 4.60-4.50 (m, 1H), 4.38 (d, J = 4.0 Hz, 2H), 4.15 (br, 2H, 2.42-2.35 (m, 12H) |

-continued

| Example | Chemical structure | Yield | NMR spectrum data |
|---|---|---|---|
| 47 | (structure) | 90% | $^1$H NMR (400 MHz, CDCl$_3$); δ 7.64 (d, J = 1.2 Hz, 1H), 7.27-7.24 (m, 1H), 7.00 (d, J = 8.0 Hz, 1H), 6.38 (s, 1H), 5.50-5.45 (m, 0.5H), 5.36-5.31 (m, 0.5H), 4.87-4.85 (m, 1H), 4.63-4.54 (m, 2H), 4.53-4.38 (m, 5H), 2.42-2.35 (m, 12H) |
| 48 | (structure) | 75% | $^1$H NMR (400 MHz, CDCl$_3$); δ 7.65 (s, 1H), 7.26-7.23 (m, 1H), 7.00-6.98 (m, 1H), 6.43 (s, 1H), 4.89-4.87 (m, 1H), 4.44-3.99 (m, 4H), 4.37 (d, J = 4.0 Hz, 2H), 3.84 (d, J = 5.6, 2H), 2.92-2.85 (m, 1H), 2.41-2.35 (m, 12H) |

Test Example 1: Preparation of Gastric Vesicles

Gastric vesicles used in the experiment were prepared by separation from porcine gastric mucosa according to a centrifugation method [Saccomani G, et al., A Nonelectrogenic H$^+$ Pump in Plasma Membranes of Hog Stomach, *J Biol* Chem., 1976, 251 (23), 7690-8]. Next, the protein content of the gastric vesicles was quantified using a bicinchoninic acid kit [Smith P K, et al., Measurement of protein using bicinchoninic acid, *Anal* Biochem., 1985, 150 (1), 76-85)].

Test Example 2: Measurement of Inhibitory Effects Against Proton Pump (H$^+$/K$^+$-ATPase) Activity The inhibitory effects of the compounds against proton pump activity were calculated based on the pump activity determined in the presence of K$^+$ ions excluding the pump activity determined in the absence of K$^+$ ions. The inhibitory effects against proton pump activity were measured in 96-well plates, and all reactions were performed with a reaction volume of 100 μm at 37° C. Specifically, 10 μm of valinomycin and each concentration of each compound were pre-incubated in a reaction buffer (50 mmol/L Tris-Hepes buffer, pH 6.4) containing porcine gastric vesicles for 15 minutes. For negative and positive control groups, 1% DMSO was added to buffer, and for test groups, 1% DMSO and a dilution of each concentration of each compound were added. Next, 0.2 mmol/L of adenosine triphosphate (ATP) was added to the reaction buffer and incubated at 37° C. for 40 minutes. After completion of the incubation, a malachite green solution was added to the reaction buffer and incubated for 30 minutes, and the amount of inorganic phosphate in the reaction buffer was measured by colorimetry using a malachite green phosphate assay Kit (Bioassay Systems). For colorimetry, the OD (optical density) at 620 nm was measured using a microplate reader [Synergy H4, hybrid multimode microplate reader, BioTek]. The percent inhibition of proton pump (H$^+$/K$^+$-ATPase) was determined based on the OD value of the control group and the OD values of various concentrations of the test compounds, and the IC$_{50}$ of each test compound was calculated using the Logistic 4-parameter function of Sigmaplot 8.0 program. The results are shown in Table 2 below.

TABLE 2

| Example | IC$_{50}$ (μM) |
|---|---|
| 1 | 0.020 |
| 2 | 0.128 |
| 3 | 0.090 |
| 4 | 0.093 |
| 5 | 0.117 |
| 6 | 0.017 |
| 7 | 0.055 |
| 8 | 0.096 |
| 9 | 0.069 |
| 10 | 0.048 |
| 11 | 0.039 |
| 12 | 0.065 |
| 13 | 0.119 |
| 14 | 0.104 |
| 15 | 0.072 |
| 16 | 0.122 |
| 17 | 0.180 |
| 18 | 0.140 |
| 19 | 0.117 |
| 20 | 0.046 |
| 21 | 0.600 |
| 22 | 0.079 |
| 23 | 0.374 |
| 27 | 0.135 |

TABLE 2-continued

| Example | IC$_{50}$ (μM) |
|---|---|
| 28 | 0.103 |
| 29 | 0.645 |
| 30 | 0.271 |
| 31 | 0.662 |
| 32 | 0.187 |
| 33 | 0.143 |
| 34 | 0.028 |
| 35 | 0.016 |
| 36 | 0.029 |
| 37 | 0.021 |
| 38 | 0.041 |
| 39 | 0.024 |
| 40 | 0.134 |
| 41 | 0.149 |
| 42 | 0.085 |
| 43 | 0.174 |
| 44 | 0.061 |
| 45 | 0.081 |
| 46 | 0.163 |
| 47 | 0.624 |
| 48 | 0.102 |

As can be seen in Table 2 above, the compounds of the present disclosure have excellent inhibitory effects against gastric H$^+$/K$^+$-ATPase.

Test Example 3: Inhibitory Effects against Esophageal Injury in Reflux Esophagitis Models The inhibitory effects of the compounds of the present disclosure against esophageal injury in reflux esophagitis models were evaluated according to the method of Nakamura [Nakamura K, et al., Effects of sodium polyacrylate (PANa) on acute esophagitis by gastric juice in rats, *Jpn J Pharmacology*, 1982, 32, 445-56].

Male Sprague Dawley (SD) rats (weighing 180-210 g) were divided into X groups (n=6) and fasted without water for 24 hours. Then, the control group was administered orally with only 10% DMSO, 10% Cremophor EL and 80% water, and the other groups were administered orally with 2 mg/kg/2 ml of each test compound together with 10% DMSO, 10% Cremophor EL and 80% water. At 1 hour after administration of the excipients and each compound, the abdominal cavity of each rate was incised under isoflurane anesthesia, and the pylorus was ligated, and the boundary between the anterior portion and the body was also ligated. At 6 hours after ligation, the test animals were euthanized, and the esophagus ranging from the thyroid to the cardiac portion was carefully extracted. The extracted esophagus was incised in a longitudinal direction and spread so as to expose the mucosa and was then fixed, after which the area of esophageal injury was measured. The results are shown in Table 3 below.

Percent (%) inhibitory activity of test compounds={(total esophageal injury area of control group−esophageal injury area of group treated with test compound)/total esophageal injury area of control group}×100.

TABLE 3

| Example | GERD (rat/mpk) |
|---|---|
| 1 | 84.0% |
| 6 | 100.0% |
| 7 | 100.0% |
| 8 | 95.4% |
| 9 | 77.2% |
| 11 | 97.6% |

TABLE 3-continued

| Example | GERD (rat/mpk) |
|---|---|
| 33 | 92.7% |
| 34 | 91.4% |
| 36 | 98.2% |
| 39 | 98.4% |

As can be seen in Table 3 above, the compounds of the present disclosure have strong inhibitory effects against esophageal injury in reflux esophagitis models.

Test Example 4: Inhibitory Effects against Histamine-Stimulated Gastric Acid Secretion in Pylorus-Ligated Rats The inhibitory effects of the compounds of the present disclosure against histamine-stimulated gastric acid secretion were evaluated using Shay's rat models [Shay H, et al. A simple method for the uniform production of gastric ulceration in the rat, Gastroenterology, 1945, 5, 43-61].

Male Sprague-Dawley (SD) rats (weighing 180-210 g) were divided into X groups (n=7) and fasted with only water access for 24 hours. At 1 hour before pylorus ligation, the control group was administered orally with only 10% DMSO, 10% Cremophor EL and 80% water, and the other groups were administered orally with 2 mg/kg/2 ml of each compound together with 10% DMSO, 10% Cremophor EL and 80% water. The abdominal cavity of each rate was incised under isoflurane anesthesia, and the pylorus was ligated. Immediately after ligation, histamine 2HCl was administered subcutaneously to each rat at a dose of 30 mg/kg/10 ml. At 3 hours after ligation, the test animals were euthanized, and the gastric content was extracted. The extracted gastric content was centrifuged at 3,000×g for 10 minutes, and the supernatant was collected to obtain gastric juice. Next, the acidity of the gastric juice was determined based on the volume of (ueq/ml) of 0.1 N—NaOH required for automatic titration of the gastric juice to pH 7.0, and the acidity of the gastric juice was multiplied by the amount of the gastric juice to determine total acid output. The results are shown in Table 4 below.

Percent (%) inhibitory activity of test compounds={(total acid output in control group−total acid output in group treated with test compound)/total acid output in control group}×100.

TABLE 4

| Example | acid output (rat/2 mpk) |
|---|---|
| 1 | 71% |
| 6 | 94% |
| 7 | 91% |
| 11 | 78% |

As can be seen in Table 4 above, the compounds of the present disclosure have string inhibitory activities against histamine-stimulated gastric acid secretion in pylorus-ligated rats.

Test Example 5: Inhibition of Acid Secretion in Lumen-Perfused Rats

The inhibitory effects of the compounds of the present disclosure against histamine-stimulated gastric acid secretion in lumen-perfused rat models were evaluated using the method of Ghosh & Schild [Ghosh M N, et al. Continuous recording of acid gastric secretion in the rat, *Br J Pharmacol Chemother*., 1958, 13 (1), 54-61].

Male Sprague-Dawley (SD) rats (weighing 250-300 g) were divided into X groups (n=4) and fasted with only water access for 24 hours. Each of the rats was anesthetized by intra-abdominal administration of urethane (1.2 g/kg), and then the abdominal cavity was incised, and the boundary between the boundary between the anterior portion and the body was ligated. A silicone tube was inserted between the stomach and the esophagus so that saline (pH 5.0) would be perfused. Furthermore, a silicone tube was inserted between the pylorus and the duodenum so that the perfusate that passed through the stomach flowed out. Then, histamine 2HCl (8 mg/kg) was infused through the jugular vein to stabilize the gastric pH. After pH stabilization, the control group was administered intravenously with only 10% DMSO, 10% Cremophor EL and 80% water, and the other groups were administered intravenously with 2 mg/kg/2 ml of each compound together with 10% DMSO, 10% Cremophor EL and 80% water. After drug administration, the perfusate was collected at 10-minute intervals for 5 hours, and the pH thereof was measured. The results are shown in FIG. 1.

As can be seen in FIG. 1, the compounds of the present disclosure have strong and long-lasting inhibitory activities against histamine-stimulated gastric acid secretion in lumen-perfused rats.

The invention claimed is:
1. An imidazo[1,2-a]pyridine derivative represented by the following formula 1 or a pharmaceutically acceptable salt thereof:

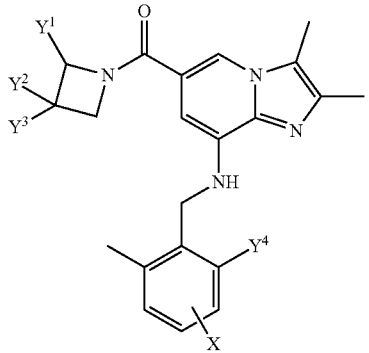

Formula 1 wherein
$Y^1$, $Y^2$ and $Y^3$ are each independently H, halogen, a $C_1$-$C_6$ straight chain alkyl unsubstituted or substituted with $R^1$, or hydroxy;
$R^1$ is hydroxy;
$Y^4$ is H, $C_1$-$C_6$ straight chain alkyl, or $C_1$-$C_6$ alkoxy; and
X is H or halogen.
2. The imidazo[1,2-a]pyridine derivative or the pharmaceutically acceptable salt thereof according to claim 1, wherein
$Y^1$ is H or a $C_1$-$C_3$ straight chain alkyl substituted with $R^1$;
$Y^2$ and $Y^3$ are each independently H, F, a $C_1$-$C_3$ straight chain alkyl unsubstituted or substituted with $R^1$ or hydroxy;
$R^1$ is hydroxy;
$Y^4$ is H, $C_1$-$C_3$ straight chain alkyl, or $C_1$-$C_3$ alkoxy; and
X is H, F, or Cl.

3. The imidazo[1,2-a]pyridine derivative or the pharmaceutically acceptable salt thereof according to claim 2, wherein
y is H;
$Y^2$ and $Y^3$ are each independently H, F, a $C_1$-$C_2$ straight chain alkyl unsubstituted or substituted with $R^1$, or hydroxy;
$R^1$ is hydroxy;
$Y^4$ is H or $C_1$-$C_2$ straight chain alkyl; and
X is H or F.
4. The imidazo[1,2-a]pyridine derivative or the pharmaceutically acceptable salt thereof according to claim 3, wherein
$Y^1$ is H;
$Y^2$ and $Y^3$ are each independently H, F, methyl, hydroxymethyl, or hydroxy;
$Y^4$ is H or methyl; and
X is H or F.
5. The imidazo[1,2-a]pyridine derivative or the pharmaceutically acceptable salt thereof according to claim 1, wherein the derivative represented by formula 1 is selected from the group consisting of the following compounds:
1) {8-[(2,6-dimethylbenzyl)amino]-2,3-dimethylimidazo[1,2-a]pyridin-6-yl}(3-hydroxyazetidin-1-yl)methanone;
6) azetidin-1-yl{8-[(2,6-dimethylbenzyl)amino]-2,3-dimethylimidazo[1,2-a]pyridin-6-yl}methanone;
7) {8-[(2,6-dimethyl)benzyl)amino]-2,3-dimethylimidazo[1,2-a]pyridin-6-yl}(3-fluoroazetidin-1-yl)methanone;
8) {8-[(2,6-dimethylbenzyl)amino]-2,3-dimethylimidazo[1,2-a]pyridin-6-yl}(3-methylazetidin-1-yl)methanone;
9) {8-[(2,6-dimethylbenzyl)amino]-2,3-dimethylimidazo[1,2-a]pyridin-6-yl}(3-hydroxy-3-methylazetidin-1-yl)methanone;
11) {8-[(2,6-dimethylbenzyl)amino]-2,3-dimethylimidazo[1,2-a]pyridin-6-yl}[3-(hydroxymethyl)azetidin-1-yl]methanone;
17) {8-[(2,6-dimethylbenzyl)amino]-2,3-dimethylimidazo [1,2-a]pyridin-6-yl}[2-(hydroxymethyl)azetidin-1-yl]methanone;
20) {8-[(2,6-dimethylbenzyl)amino]-2,3-dimethylimidazo[1,2-a]pyridin-6-yl}[3-(2-hydroxyethyl)azetidin-1-yl]methanone;
23) {2,3-dimethyl-8-[(2-methylbenzyl)amino]imidazo[1,2-a]pyridin-6-yl}(3-hydroxyazetidin-1-yl)methanone;
24) {8-[(5-fluoro-2-methylbenzyl)amino]-2,3-dimethylimidazo[1,2-a]pyridin-6-yl}(3-hydroxyazetidin-1-yl)methanone;
25) (3-hydroxyazetidin-1-yl){8-[(2-methoxy-6-methylbenzyl)amino]-2,3-dimethylimidazo[1,2-a]pyridin-6-yl)methanone;
26) [3-(hydroxymethyl)azetidin-1-yl]{8-[(2-methoxy-6-methylbenzyl)amino]-2,3-dimethylimidazo[1,2-a]pyridin-6-yl)}methanone;
27) {8-[(4-fluoro-2-methylbenzyl)amino]-2,3-dimethylimidazo[1,2-a]pyridin-6-yl}(3-hydroxyazetidin-1-yl)methanone;
28) azetidin-1-yl {8-[(4-fluoro-2-methylbenzyl)amino]-2,3-dimethylimidazo[1,2-a]pyridin-6-yl)}methanone;
29) {8-[(4-fluoro-2-methylbenzyl)amino]-2,3-dimethylimidazo[1,2-a]pyridin-6-yl}(3-fluoroazetidin-1-yl)methanone;
30) {8-[(4-fluoro-2-methylbenzyl)amino]-2,3-dimethylimidazo[1,2-a]pyridin-6-yl}(3-methylazetidin-1-yl)methanone;

31) {8-[(4-fluoro-2-methylbenzyl)amino]-2,3-dimethylimidazo[1,2-a]pyridin-6-yl}(3-hydroxy-3-methylazetidine-1-yl)methanone;
33) {8-[(4-fluoro-2-methylbenzyl)amino]-2,3-dimethylimidazo[1,2-a]pyridin-6-yl}(3-(hydroxymethyl)azetidin-1-yl)methanone;
34) {8-[(4-fluoro-2,6-dimethylbenzyl)amino]-2,3-dimethylimidazo[1,2-a]pyridin-6-yl}(3-hydroxyazetidin-1-yl)methanone;
35) azetidin-1-yl{8-[(4-fluoro-2,6-dimethylbenzyl)amino]-2,3-dimethylimidazo[1,2-a]pyridin-6-yl}methanone;
36) {8-[(4-fluoro-2,6-dimethylbenzyl)amino]-2,3-dimethylimidazo[1,2-a]pyridin-6-yl}(3-fluoroazetidin-1-yl)methanone;
37) {8-[(4-fluoro-2,6-dimethylbenzyl)amino]-2,3-dimethylimidazo[1,2-a]pyridin-6-yl}(3-methylazetidin-1-yl)methanone;
38) {8-[(4-fluoro-2,6-dimethylbenzyl)amino]-2,3-dimethylimidazo[1,2-a]pyridin-6-yl}(3-hydroxy-3-methylazetidin-1-yl)methanone;
39) {8-[(4-fluoro-2,6-dimethylbenzyl)amino]-2,3-dimethylimidazo[1,2-a]pyridin-6-yl}[3-(hydroxymethyl)azetidin-1-yl]methanone;
41) {8-[(3-fluoro-2,6-dimethylbenzyl)amino]-2,3-dimethylimidazo[1,2-a]pyridin-6-yl}(3-hydroxyazetidin-1-yl)methanone;
42) azetidin-1-yl{8-[(3-fluoro-2,6-dimethylbenzyl)amino]-2,3-dimethylimidazo[1,2-a]pyridin-6-yl}methanone;
43) {8-[(3-fluoro-2,6-dimethylbenzyl)amino]-2,3-dimethylimidazo[1,2-a]pyridin-6-yl}(3-fluoroazetidin-1-yl)methanone;
44) {8-[(3-fluoro-2,6-dimethylbenzyl)amino]-2,3-dimethylimidazo[1,2-a]pyridin-6-yl}[3-(hydroxymethyl)azetidin-1-yl]methanone;
45) azetidin-1-yl{8-[(3-chloro-2,6-dimethylbenzyl)amino]-2,3-dimethylimidazo[1,2-a]pyridin-6-yl}methanone;
46) {8-[(3-chloro-2,6-dimethylbenzyl)amino]-2,3-dimethylimidazo[1,2-a]pyridin-6-yl}(3-hydroxyazetidin-1-yl]methanone;
47) {8-[(3-chloro-2,6-dimethylbenzyl)amino]-2,3-dimethylimidazo[1,2-a]pyridin-6-yl}(3-fluoroazetidin-1-yl)methanone; and
48) {8-[(3-chloro-2,6-dimethylbenzyl)amino]-2,3-dimethylimidazo[1,2-a]pyridin-6-yl}[3-(hydroxymethyl)azetidin-1-yl]methanone.

6. A pharmaceutical composition for treating gastrointestinal inflammatory disease or a gastric acid-related disease, the composition containing, as an active ingredient, an imidazo[1,2-a]pyridine derivative or a pharmaceutically acceptable salt thereof according to claim 1.

7. The pharmaceutical composition of claim 6, wherein the gastrointestinal inflammatory disease or the gastric acid-related disease is selected from the group consisting of peptic ulcer, gastric and duodenal ulcer, nonsteroidal anti-inflammatory drug (NSAID)-induced ulcer, *Helicobacter pylori* infection, functional indigestion, Zollinger-Ellison syndrome, gastritis, gastroesophageal reflux disease (GERD), and nonerosive reflux disease (NERD).

8. A method for treating a disease caused by excessive secretion of gastric acid, the method comprising administering a therapeutically effective amount of an imidazo[1,2-a]pyridine derivative or a pharmaceutically acceptable salt thereof according to claim 1.

* * * * *

UNITED STATES PATENT AND TRADEMARK OFFICE
CERTIFICATE OF CORRECTION

PATENT NO. : 10,696,671 B2
APPLICATION NO. : 16/314749
DATED : June 30, 2020
INVENTOR(S) : Jeongmin Kim et al.

Page 1 of 1

It is certified that error appears in the above-identified patent and that said Letters Patent is hereby corrected as shown below:

In the Claims

Column 44, Line 4:
In Claim 3, delete "y" and insert -- $Y^1$ --, therefor.

Column 44, Line 28:
In Claim 5, delete "{8-[(2,6-dimethyl)benzyl)amino]" and insert
-- {8-[(2,6-dimethylbenzyl)amino] --, therefor.

Column 44, Line 56:
In Claim 5, delete "-yl)" and insert -- -yl --, therefor.

Column 44, Line 61:
In Claim 5, delete "-yl)" and insert -- -yl --, therefor.

Signed and Sealed this
Sixth Day of October, 2020

Andrei Iancu
*Director of the United States Patent and Trademark Office*